(12) United States Patent
Jaggi et al.

(10) Patent No.: US 9,687,174 B2
(45) Date of Patent: Jun. 27, 2017

(54) MEDICAL DEVICE POSITION GUIDANCE SYSTEM WITH WIRELESS CONNECTIVITY BETWEEN A NONINVASIVE AND AN INVASIVE DEVICE

(75) Inventors: David S. Jaggi, Oak Park, IL (US); Donald A. Kay, Sharon, MA (US); Joseph P. Killam, Wonder Lake, IL (US); Salvatore Manzella, Jr., Barrington, IL (US); King Y. Moy, Tinley Park, IL (US); David K. Platt, Mt. Prospect, IL (US); Shawn G. Purnell, Palatine, IL (US); Alan R. Shapiro, Sharon, MA (US); Michael C. Shaughnessy, Arlington Heights, IL (US); Mark C. Witt, Chicago, IL (US); Christopher Zachara, Lake Bluff, IL (US)

(73) Assignee: Corpak Medsystems, Inc., Buffalo Grove, IL (US)

( * ) Notice: Subject to any disclaimer, the term of this patent is extended or adjusted under 35 U.S.C. 154(b) by 0 days.

(21) Appl. No.: 13/472,588

(22) Filed: May 16, 2012

(65) Prior Publication Data

US 2012/0226148 A1 Sep. 6, 2012

Related U.S. Application Data

(63) Continuation of application No. 11/530,385, filed on Sep. 8, 2006, now Pat. No. 8,197,494.

(51) Int. Cl.
*A61B 5/06* (2006.01)
*A61B 5/07* (2006.01)

(52) U.S. Cl.
CPC ............... *A61B 5/06* (2013.01); *A61B 5/061* (2013.01); *A61B 5/062* (2013.01); *A61B 5/065* (2013.01); *A61B 5/07* (2013.01)

(58) Field of Classification Search
USPC .......................................... 600/424; 606/130
See application file for complete search history.

(56) References Cited

U.S. PATENT DOCUMENTS

| 921,368 A | 5/1909 | Crook |
|---|---|---|
| 1,074,706 A | 10/1913 | Ferguson |

(Continued)

FOREIGN PATENT DOCUMENTS

| AU | 642647 | 10/1993 |
|---|---|---|
| AU | PQ 9592 | 8/2000 |

(Continued)

OTHER PUBLICATIONS

Radio propagation by Wikipedia, pub. online on Aug. 30, 2006 url: https://en.wikipedia.org/w/index.php?title=Radio_propagation&oldid=72911135.*

(Continued)

*Primary Examiner* — Katherine Fernandez
*Assistant Examiner* — Michael Kellogg
(74) *Attorney, Agent, or Firm* — Dority & Manning, P.A.

(57) ABSTRACT

A medical device position guidance system having a noninvasive medical device communicable with an invasive medical device. The system provides outputs useful to assess the position of an invasive medical device in an animal, such as a human. A magnetic field is used to gather information about the position of the invasive device. Radio waves are used to communicate this information between the noninvasive device and the invasive device.

7 Claims, 22 Drawing Sheets

(56) References Cited

U.S. PATENT DOCUMENTS

| | | |
|---|---|---|
| 2,103,050 A | 12/1937 | White |
| 2,321,355 A | 1/1942 | Berman |
| 2,521,745 A | 9/1950 | Pope |
| 2,820,959 A | 1/1958 | Bell |
| 2,863,458 A | 12/1958 | Modny et al. |
| 2,906,944 A | 9/1959 | Lebourg |
| 2,908,863 A | 10/1959 | Neff |
| 2,941,822 A | 6/1960 | Moecker |
| 2,949,910 A | 8/1960 | Brown et al. |
| 3,042,030 A | 7/1962 | Read |
| 3,043,309 A | 7/1962 | McCarthy |
| 3,190,290 A | 6/1965 | Alley et al. |
| 3,253,588 A | 5/1966 | Vuilleumier et al. |
| 3,452,742 A | 7/1969 | Muller |
| 3,471,773 A | 10/1969 | Penland |
| 3,547,103 A | 12/1970 | Cook |
| 3,597,680 A | 8/1971 | Haddon |
| 3,605,750 A | 9/1971 | Sheridan et al. |
| 3,617,865 A | 11/1971 | Hakata |
| 3,618,614 A | 11/1971 | Flynn |
| 3,622,784 A | 11/1971 | Del Guercio |
| 3,623,101 A | 11/1971 | Grebe et al. |
| 3,625,200 A | 12/1971 | Muller |
| 3,645,562 A | 2/1972 | Fandetti et al. |
| 3,653,050 A | 3/1972 | Eggleston, Jr. |
| 3,656,161 A | 4/1972 | MacPherson |
| 3,659,588 A | 5/1972 | Kahn et al. |
| 3,661,148 A | 5/1972 | Kolin |
| 3,667,781 A | 6/1972 | Holbrook |
| 3,731,684 A | 5/1973 | Spiegel |
| 3,749,086 A | 7/1973 | Kline et al. |
| 3,749,134 A | 7/1973 | Slingluff et al. |
| 3,794,041 A | 2/1974 | Frei et al. |
| 3,831,086 A | 8/1974 | Pesto |
| 3,932,805 A | 1/1976 | Abe et al. |
| 4,173,228 A | 11/1979 | Van Steenwyk et al. |
| 4,317,078 A | 2/1982 | Weed et al. |
| 4,379,261 A | 4/1983 | Lakin |
| 4,380,726 A * | 4/1983 | Sado .................. G01R 31/36 320/DIG. 21 |
| 4,445,089 A | 4/1984 | Harrison |
| 4,538,836 A | 9/1985 | Krutten |
| 4,557,261 A | 12/1985 | Rugheimer |
| 4,572,198 A | 2/1986 | Codrington |
| 4,809,713 A | 3/1989 | Grayzel |
| 4,905,698 A | 3/1990 | Strohl, Jr. et al. |
| 4,940,052 A * | 7/1990 | Mann et al. .................. 607/17 |
| 4,998,932 A | 3/1991 | Rosen et al. |
| 5,005,592 A | 4/1991 | Cartmell |
| 5,014,008 A | 5/1991 | Flowerdew |
| 5,042,486 A | 8/1991 | Pfeiler et al. |
| 5,045,071 A | 9/1991 | McCormick et al. |
| 5,098,378 A | 3/1992 | Piontek et al. |
| 5,099,845 A | 3/1992 | Besz et al. |
| 5,104,157 A | 4/1992 | Bahner |
| 5,125,915 A | 6/1992 | Berry et al. |
| 5,183,045 A | 2/1993 | Takamura et al. |
| 5,196,796 A | 3/1993 | Misic et al. |
| 5,211,165 A | 5/1993 | Dumoulin et al. |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,265,610 A | 11/1993 | Darrow et al. |
| 5,273,025 A | 12/1993 | Sakiyama et al. |
| 5,279,607 A | 1/1994 | Schentag et al. |
| 5,325,873 A | 7/1994 | Hirschi et al. |
| 5,353,807 A | 10/1994 | DeMarco |
| 5,375,596 A | 12/1994 | Twiss et al. |
| 5,377,678 A | 1/1995 | Dumoulin et al. |
| 5,386,828 A | 2/1995 | Owens et al. |
| 5,391,199 A | 2/1995 | Ben-Haim |
| 5,395,366 A | 3/1995 | D'Andrea et al. |
| 5,425,367 A * | 6/1995 | Shapiro et al. .................. 600/424 |
| 5,429,132 A | 7/1995 | Guy et al. |
| 5,437,277 A | 8/1995 | Dumoulin et al. |
| 5,443,066 A | 8/1995 | Dumoulin et al. |
| 5,443,489 A | 8/1995 | Ben-Haim |
| 5,445,150 A | 8/1995 | Dumoulin et al. |
| 5,480,422 A | 1/1996 | Ben-Haim |
| 5,513,637 A | 5/1996 | Twiss et al. |
| 5,543,489 A | 8/1996 | Ben-Haim |
| 5,558,091 A | 9/1996 | Acker et al. |
| 5,584,838 A | 12/1996 | Rona et al. |
| 5,592,939 A | 1/1997 | Martinelli |
| 5,603,697 A | 2/1997 | Grundy et al. |
| 5,622,169 A | 4/1997 | Golden et al. |
| 5,645,065 A | 7/1997 | Shapiro et al. |
| 5,669,383 A | 9/1997 | Johnson |
| 5,699,801 A | 12/1997 | Atalar et al. |
| 5,711,299 A | 1/1998 | Manwaring et al. |
| 5,713,946 A | 2/1998 | Ben-Haim |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,738,096 A | 4/1998 | Ben-Haim |
| 5,752,513 A | 5/1998 | Acker et al. |
| 5,762,064 A | 6/1998 | Polvani |
| 5,769,843 A | 6/1998 | Abela et al. |
| 5,792,055 A | 8/1998 | McKinnon |
| 5,795,298 A | 8/1998 | Vesely et al. |
| 5,797,849 A | 8/1998 | Vesely et al. |
| 5,803,089 A | 9/1998 | Ferre et al. |
| 5,810,728 A | 9/1998 | Kuhn |
| 5,817,022 A | 10/1998 | Vesely |
| 5,827,202 A | 10/1998 | Miraki et al. |
| 5,830,144 A | 11/1998 | Vesely |
| 5,833,608 A | 11/1998 | Acker |
| 5,840,024 A | 11/1998 | Taniguchi et al. |
| 5,840,025 A | 11/1998 | Ben-Haim |
| 5,843,002 A | 12/1998 | Pecor et al. |
| 5,846,198 A | 12/1998 | Killmann |
| 5,868,673 A | 2/1999 | Vesely |
| 5,868,674 A | 2/1999 | Glowinski et al. |
| 5,879,297 A | 3/1999 | Haynor et al. |
| 5,882,304 A | 3/1999 | Ehnholm et al. |
| 5,899,860 A | 5/1999 | Pfeiffer et al. |
| 5,902,238 A | 5/1999 | Golden et al. |
| 5,906,579 A | 5/1999 | Vander Salm et al. |
| 5,913,820 A | 6/1999 | Bladen et al. |
| 5,916,162 A | 6/1999 | Snelton et al. |
| 5,936,406 A | 8/1999 | Potthast |
| 5,938,603 A | 8/1999 | Ponzi |
| 5,941,858 A | 8/1999 | Johnson |
| 5,944,023 A | 8/1999 | Johnson et al. |
| 5,951,472 A | 9/1999 | Van Vaals et al. |
| 5,954,665 A | 9/1999 | Ben-Haim |
| 5,964,757 A | 10/1999 | Ponzi |
| 5,997,473 A | 12/1999 | Taniguchi et al. |
| 6,009,878 A | 1/2000 | Weijand et al. |
| 6,014,580 A | 1/2000 | Blume et al. |
| 6,019,725 A | 2/2000 | Vesely et al. |
| 6,019,727 A | 2/2000 | Koger et al. |
| 6,023,636 A | 2/2000 | Wendt et al. |
| 6,024,739 A | 2/2000 | Ponzi et al. |
| 6,047,214 A | 4/2000 | Mueller et al. |
| 6,052,610 A | 4/2000 | Koch |
| 6,059,718 A | 5/2000 | Taniguchi et al. |
| 6,064,905 A | 5/2000 | Webster et al. |
| 6,066,094 A | 5/2000 | Ben-Haim |
| 6,073,043 A | 6/2000 | Schneider |
| 6,076,007 A | 6/2000 | England et al. |
| 6,087,831 A | 7/2000 | Bornert et al. |
| 6,104,944 A | 8/2000 | Martinelli |
| 6,112,111 A | 8/2000 | Glantz |
| 6,129,668 A | 10/2000 | Haynor et al. |
| 6,161,032 A | 12/2000 | Acker |
| 6,173,199 B1 | 1/2001 | Gabriel |
| 6,185,448 B1 | 2/2001 | Borovsky |
| 6,190,382 B1 | 2/2001 | Ormsby et al. |
| 6,198,963 B1 | 3/2001 | Haim et al. |
| 6,201,387 B1 | 3/2001 | Govari |

(56) References Cited

U.S. PATENT DOCUMENTS

| | | | |
|---|---|---|---|
| 6,201,987 | B1 | 3/2001 | Dumoulin |
| 6,203,493 | B1 | 3/2001 | Ben-Haim |
| 6,211,666 | B1 | 4/2001 | Acker |
| 6,216,026 | B1 | 4/2001 | Kuhn et al. |
| 6,216,027 | B1 | 4/2001 | Willis et al. |
| 6,216,028 | B1 | 4/2001 | Haynor et al. |
| 6,223,066 | B1 | 4/2001 | Govari |
| 6,226,547 | B1 | 5/2001 | Lockhart et al. |
| 6,230,038 | B1 | 5/2001 | von Gutfeld et al. |
| 6,230,042 | B1 | 5/2001 | Slettenmark |
| 6,233,476 | B1 | 5/2001 | Strommer et al. |
| 6,235,038 | B1 | 5/2001 | Hunter et al. |
| 6,236,879 | B1 | 5/2001 | Konings |
| 6,246,231 | B1 | 6/2001 | Ashe |
| 6,263,230 | B1 | 7/2001 | Haynor et al. |
| 6,266,551 | B1 | 7/2001 | Osadchy et al. |
| 6,272,370 | B1 | 8/2001 | Gillies et al. |
| 6,298,257 | B1 | 10/2001 | Hall et al. |
| 6,298,261 | B1 | 10/2001 | Rex |
| 6,304,769 | B1 | 10/2001 | Arenson et al. |
| 6,364,867 | B2 | 4/2002 | Wise et al. |
| 6,366,799 | B1 | 4/2002 | Acker et al. |
| 6,374,134 | B1 | 4/2002 | Bladen et al. |
| 6,381,485 | B1 | 4/2002 | Hunter et al. |
| 6,427,079 | B1 | 7/2002 | Schneider et al. |
| 6,432,041 | B1 | 8/2002 | Taniguchi et al. |
| 6,445,943 | B1 | 9/2002 | Ferre et al. |
| 6,473,635 | B1 | 10/2002 | Rasche |
| 6,474,341 | B1 * | 11/2002 | Hunter et al. ............... 128/899 |
| 6,544,251 | B1 | 4/2003 | Crawford |
| 6,553,326 | B1 | 4/2003 | Kirsch et al. |
| 6,574,498 | B1 | 6/2003 | Gilboa |
| 6,608,688 | B1 | 8/2003 | Faul et al. |
| 6,618,612 | B1 | 9/2003 | Acker et al. |
| 6,687,531 | B1 | 2/2004 | Ferre et al. |
| 6,757,557 | B1 | 6/2004 | Bladen et al. |
| 6,772,002 | B2 | 8/2004 | Schmidt et al. |
| 6,774,624 | B2 | 8/2004 | Anderson et al. |
| 6,876,196 | B1 | 4/2005 | Taulin et al. |
| 6,895,267 | B2 | 5/2005 | Panescu et al. |
| 6,980,921 | B2 | 12/2005 | Anderson et al. |
| 7,004,938 | B2 | 2/2006 | Ormsby et al. |
| 7,015,859 | B2 | 3/2006 | Anderson |
| 7,096,148 | B2 | 8/2006 | Anderson et al. |
| 7,158,754 | B2 | 1/2007 | Anderson |
| 7,197,354 | B2 | 3/2007 | Sobe |
| 7,397,364 | B2 | 7/2008 | Govari |
| 7,715,898 | B2 | 5/2010 | Anderson |
| 7,822,464 | B2 | 10/2010 | Maschke et al. |
| 7,835,785 | B2 | 11/2010 | Scully et al. |
| 7,976,518 | B2 * | 7/2011 | Shaughnessy et al. ....... 604/284 |
| 2001/0045826 | A1 | 11/2001 | Schneider |
| 2002/0161306 | A1 | 10/2002 | Govari |
| 2002/0161421 | A1 | 10/2002 | Lee et al. |
| 2003/0125725 | A1 | 7/2003 | Woodard et al. |
| 2005/0228370 | A1 | 10/2005 | Sterzer et al. |
| 2005/0272975 | A1 * | 12/2005 | McWeeney ........ A61B 1/00071 600/113 |
| 2006/0159323 | A1 * | 7/2006 | Sun ..................... A61B 5/0035 382/128 |
| 2006/0173449 | A1 * | 8/2006 | Sharareh ............ A61B 18/1492 606/41 |
| 2006/0184011 | A1 | 8/2006 | Macaulay et al. |
| 2008/0004663 | A1 * | 1/2008 | Jorgenson ........................ 607/5 |

FOREIGN PATENT DOCUMENTS

| | | |
|---|---|---|
| AU | PR 5250 | 5/2001 |
| DE | 2432173 | 1/1976 |
| DE | 19830183 A1 | 7/1999 |
| EP | 91577 | 10/1983 |
| EP | 320623 | 6/1989 |
| EP | 355996 | 2/1990 |
| EP | 357397 | 3/1990 |
| EP | 0359697 B1 | 3/1990 |
| EP | 399536 | 5/1991 |
| WO | WO 88/00810 | 2/1988 |
| WO | WO 90/02514 | 3/1990 |
| WO | WO 92/03090 | 3/1992 |
| WO | WO 93/04628 | 3/1993 |
| WO | WO 96/05768 A1 | 2/1996 |
| WO | WO 96/07352 | 3/1996 |
| WO | WO 96/32060 | 10/1996 |
| WO | WO 97/29683 A1 | 8/1997 |
| WO | WO 02/15973 A1 | 2/2002 |

OTHER PUBLICATIONS

Modelling and Characterisation of Radio Propagation from Wireless Implants at Different Frequencies by Alomainy et al. pub. Wireless Technology, Sep. 10-12, 2006.*
Angioplasty by Wikipedia, pub. online on Aug. 31, 2006 url: https://en.wikipedia.org/w/index.php?title=Angioplasty &oldid=73000342.*
Radiofrequency ablation by Wikipedia, pub. online on Aug. 21, 2006 url: https://en.wikipedia.org/w/index. php?title=Radiofrequency_ablation&oldid=70877531.*
Implanted antennas inside a human body: simulations, designs, and characterizations by Kim et al. pub. Microwave Theory and Techniques, IEEE Transactions on , Issue Date: Aug. 2004.*
Broadcasting by Wikipedia, pub. online on Aug. 27, 2006, url: https://en.wikipedia.org/w/index.php?title=Broadcasting &oldid=72230474.*
American wire gauge by Wikipedia, pub. online on Nov. 5, 2016 at https://en.wikipedia.org/wiki/American_wire_gauge.*
Copper by Wikipedia, Pub. online on Aug. 31, 2006 at https://en.wikipedia.org/w/index.php?title=Copper&oldid=72943150.*
1P Series Catalog, prior to Jan. 13, 2005.
A Novel Technique for Nasoduodenal Feeding Tube Placement in Critically Ill Patients, dated Feb. 14, 2002.
Biosense Webster, A Johnson & Johnson Company, CARTO™ EP Navigation System, printed from http://www.biosensewebster.com/US/products_carton av.htm, Oct. 23, 2002.
Biosense Webster, A Johnson & Johnson Company, CUSTOMCATH™ Program, printed from http://www.biosensewebster.com/US/products.htm, Oct. 23, 2002.
CARTO™ EP Navigation System, printed from http://www.biosensewebster.com/US/products_carton av.htm, Oct. 23, 2002.
Cathlocator™ from www.micronix.com printed on Oct. 25, 2002.
"Cath-Finder™ Catheter Tracking System: a new device for positioning of central venous catheters. Early experience from implantation of brachia portal systems," by H. Starkhammar, M. Bengtsson and D.A. Kay, Acta Anaesthesiol Scand, 1990 on or before December thereof, pp. 296-300.
CF-Q160AL *innoflex*™, Olympus® Focus on Life, printed from http://www.olympusamerica.com/msg_section, Oct. 22, 2002.
CF-Q160S, EVIS EXERA™, Olympus® Focus on Life, printed from http://www.olympusamerica.com/msg_section, Oct. 22, 2002.
Department of Health and Human Services, Navi-Star Diagnostic/Ablation Deflectable Tip Catheter, Food and Drug Administration, Jun. 15, 2000.
EVIS 140 Series, printed from http://www.olympus.co.jp, Oct. 22, 2002.
EVIS 240 Series, printed from http://www.olympus.co.jp, Oct. 22, 2002.
Extender cable graphic, manufactured by LEMO USA Inc., distributed and sold by HLC Ltd. as of Jul. 29, 2002.
Flow Through Stylet Connector, Corpak MedSystems, Aug. 19, 1987.
FMN Connector Connectors for FFC, written by JST, pp. 390-391, prior to Jan. 13, 2005.
GIF-N30 Fiberscope, Olympus® focus on Live, printed from http://www.olympusamerica.com/msg_section, Oct. 22, 2002.
GIF-XP160, SlimSIGHT™, Olympus® Focus on Life, printed from http://www.olympusamerica.com/msg_section, Oct. 22, 2002.

(56) References Cited

OTHER PUBLICATIONS

LEMO's Push-Pull Self-Latching Connection System, p. 5, LEMO USA Inc., prior to Jan. 13, 2005.
Lucent® Medical Systems, Adding Intelligence to Indwelling Devices, printed from http://www.lucentmedical.com/overview2.htm., Oct. 23, 2002.
Lucent® Medical Systems, Enteral Feeding Tubes, printed from http://www.lucentmedical.com/et.htm, Oct. 23, 2002.
Lucent® Medical Systems, The LMS—Zortran™ printed from http://www.lucentmedical.com/zortran.htm, Oct. 23, 2002.
Luminal Devices, The Cathlocator: A novel non-radiological method for the localization of enteral tubes, Journal of Gastroenterology and Hepatology (1996) 11, pp. 500-505, date 1996 on or before December of such year.
Multiple Lesion™ FFR of Serial Tandem Lesions, Florence Medical, printed from http://www.florencemedical.com, Oct. 22, 2002.
NAVIGAToR®, VIASYS® Healthcare, [online] [retrieved on Aug. 30, 2006]. Retrieved from <file://C:\DOCUME~1/rys.BBL\LOCALS~1\Temp\PDDJQIEU.htm>.
NAVI-STAR® diagnostic/Ablation Deflectable Tip Catheter, U.S. Food and Drug Administration—Center for Devices and Radiological Health, printed in 2002, on or before the month of December thereof.
"NAV PICC™ and NAV PRØ-PICC™," [online] [retrieved on Aug. 30, 2006]. Retrieved from<URL: http://www.viasyshelathcare.com/prod_serv/prodDetail.aspx?config=ps_prodDtl&prodID=322>.
News from NAVION™ printed from http://www.navionbiomedical.com/system.htm, Oct. 23, 2002.
Olympus Medical Endoscope & Surgical Products, Olympus, printed from http://www.olympus.co.jp/LineUp/Endoscope/indexE.html, Oct. 17, 2002.
Olympus Medical Endoscope & Surgical Products, Olympus, printed from http://www.olympus.co.jp/en/mesg/endoscope, Oct. 22, 2002.
"PICC Placement in Humans Using Electromagnetic Detection," by Douglas Buehrle, RN, Infusion Specialist, TVAP Inc. Durham NC, 2002 on or before December thereof.
Radio-Frequency Interface—An EMC Study of the Cathlocator™, Institute of Technology, Department of Biomedical Engineering, Master's Thesis , Dec. 20, 2002.
Research in Catheter and Tube Placement, printed from http://www.navionbiomedical.com/system.htm, Oct. 23, 2002.
Selection of contact types, p. 9, LEMO USA Inc., prior to Jan. 13, 2005.
SmartFlow® Family of Product, Simultaneous CFR/FFR™, printed from http://www.florencemedical.com/aboutFlorence/history.htm, Oct. 22, 2002.
"Stent," [online] [retrieved on Sep. 5, 2006]. Retrieved from the Internet at <URL: http://www.guidant.com/condition/images/030Stent.jpg>.
The NAVION™ BioNavigation System, printed from http://www.navionbiomedical.com/system.htm, Oct. 23, 2002.
U.S. Food and Drug Administration, Section 510(k) Marketing Approval for C.R. Bard, Incorporated Sherlock™ Tip Location System, Apr. 14, 2006.

* cited by examiner

US 9,687,174 B2

MEDICAL DEVICE POSITION GUIDANCE SYSTEM WITH WIRELESS CONNECTIVITY BETWEEN A NONINVASIVE AND AN INVASIVE DEVICE

CROSS REFERENCES TO RELATED APPLICATIONS

This application is continuation that claims priority to U.S. patent application Ser. No. 11/530,385 filed on Sep. 8, 2006, the entire contents of which being incorporated herein by reference.

BACKGROUND

Physicians and other health care providers frequently use catheters to treat patients. The known catheters include a tube which is inserted into the human body. Certain catheters are inserted into through the patient's nose or mouth for treating the gastrointestinal tract. These catheters, sometimes referred to as enteral catheters, typically include feeding tubes. The feeding tube lies in the stomach or intestines, and a feeding bag delivers liquid nutrient, liquid medicine or a combination of the two to the patient.

Other types of catheters are inserted into the patient's veins or arteries for treating the cardiovascular system. These intravascular catheters include, among others, the central venous catheter, peripheral venous catheter and the peripherally inserted central catheter (PICC). These catheters include a relatively small tube that passes through the patient's veins or arteries. Depending on the application, the health care providers can use these intravascular catheters to remove blood vessel blockages, place inserts into blood vessels and to provide patients with injections of medications, drugs, fluids, nutrients, or blood products over a period of time, sometimes several weeks or more.

When using these known enteral and intravascular catheters, it is important to place the end of the catheter at the proper location within the human body. Erroneous placement of the catheter tip may injure or harm the patient. For example, if the health care provider erroneously places an enteral catheter into the patient's lungs, liquid may be introduced into the lungs with harmful results. If the health care provider erroneously places an intravascular catheter into the wrong blood vessel of the cardiovascular system, the patient may experience infection, injury or a harmful blockage.

In some cases, health care providers use X-ray machines to gather information about the location of the catheters within the body. There are several of disadvantages with using X-ray machines. For example, these machines are relatively large and heavy, consume a relatively large amount of energy and expose the patient to a relatively high degree of X-ray radiation. Also, these machines are typically not readily accessible for use because, due to their size, they are usually installed in a special X-ray room. This room can be relatively far away from the patient's room. Therefore, health care providers can find it inconvenient to use these machines for their catheter procedures. Furthermore, it can be inconvenient to transport these machines to a patient's home for home care catheter procedures.

Accordingly, there is a need to overcome or otherwise lessen the effects of such disadvantages.

SUMMARY

A medical device position guidance system having a noninvasive medical device communicable directly or indirectly with an invasive medical device. The system provides visual or audio output useful to assess the position of the invasive medical device in an animal, such as a human, with respect to the position of the noninvasive medical device. A magnetic field is used to gather information about the position of the invasive device relative to the noninvasive device. Radio waves are used to communicate this information between the noninvasive device and the invasive device.

DETAILED DESCRIPTION

I. General Overview

Figure 1:
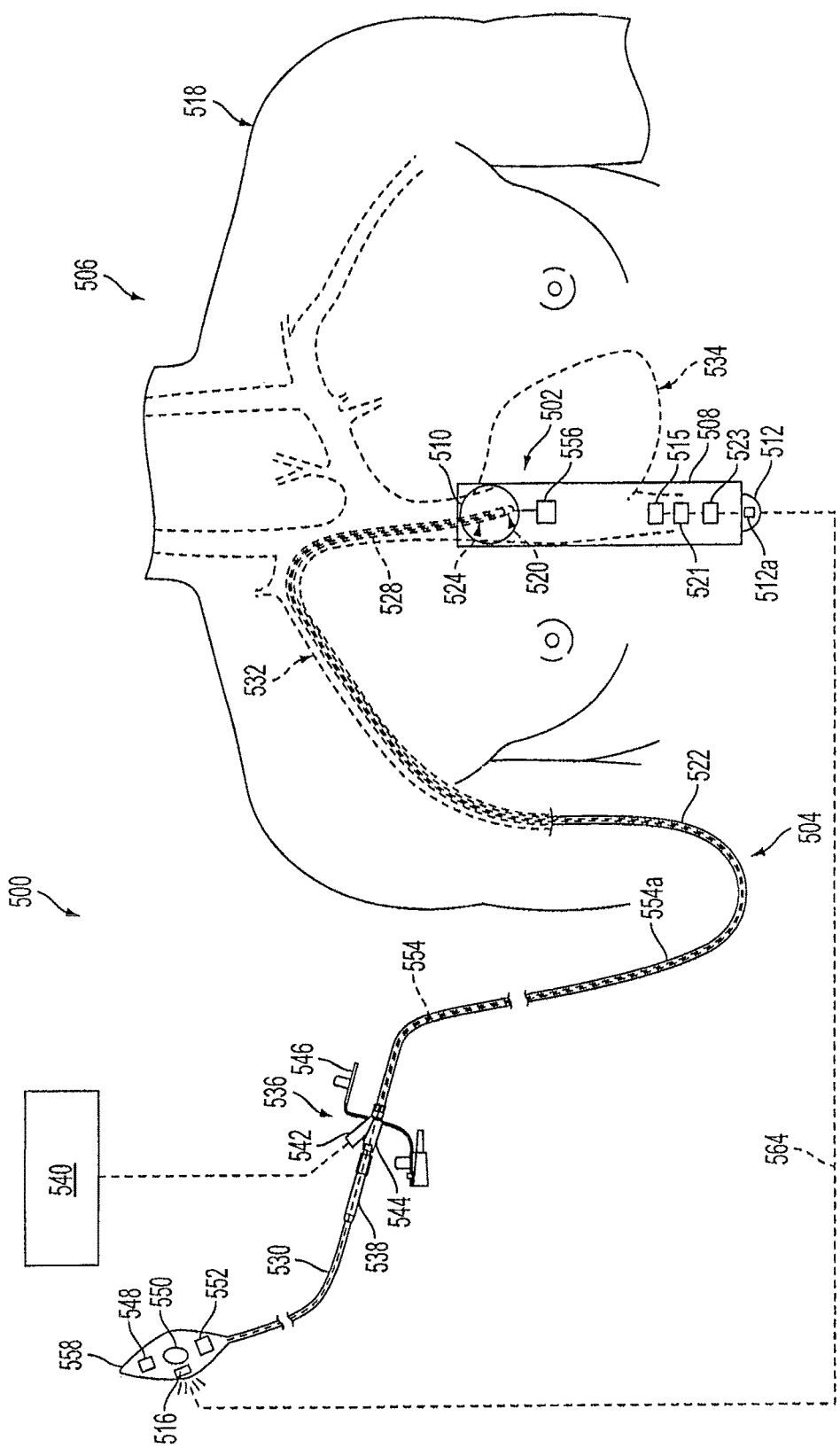
FIG. 1 is a top or plan view of the medical device position guidance system illustrating an intravenous application involving a peripherally inserted central catheter inserted into a human body and illustrating radio wave communication between the catheter assembly and the noninvasive device.

Referring now to the drawings, FIG. 1 illustrates one embodiment of a medical device position guidance system 500. The medical device position guidance system 500 includes an external device or noninvasive device 502 and a catheter assembly 504. The noninvasive device 502 is positionable over a surface of an animal, such as a human 506. Although the illustrated example depicts a human, it should be appreciated that medical device position guidance system 500 could be used with any animal such as domestic animals. In general, the noninvasive device 502 includes a noninvasive housing 508 which supports a magnetic field generator 510, and a receiver 512 including an antenna 512a operably coupled to a processor 523, where the processor 523 is coupled to a memory device 515. According to the embodiments, the medical device position guidance system 500 is operable to provide audiovisual information about the orientation of an invasive medical device and the position of the invasive medical device relative to the external device 502, through a wireless connection between the invasive medical device 504 and the noninvasive device 502.

II. Intravascular Embodiment

Figure 3:
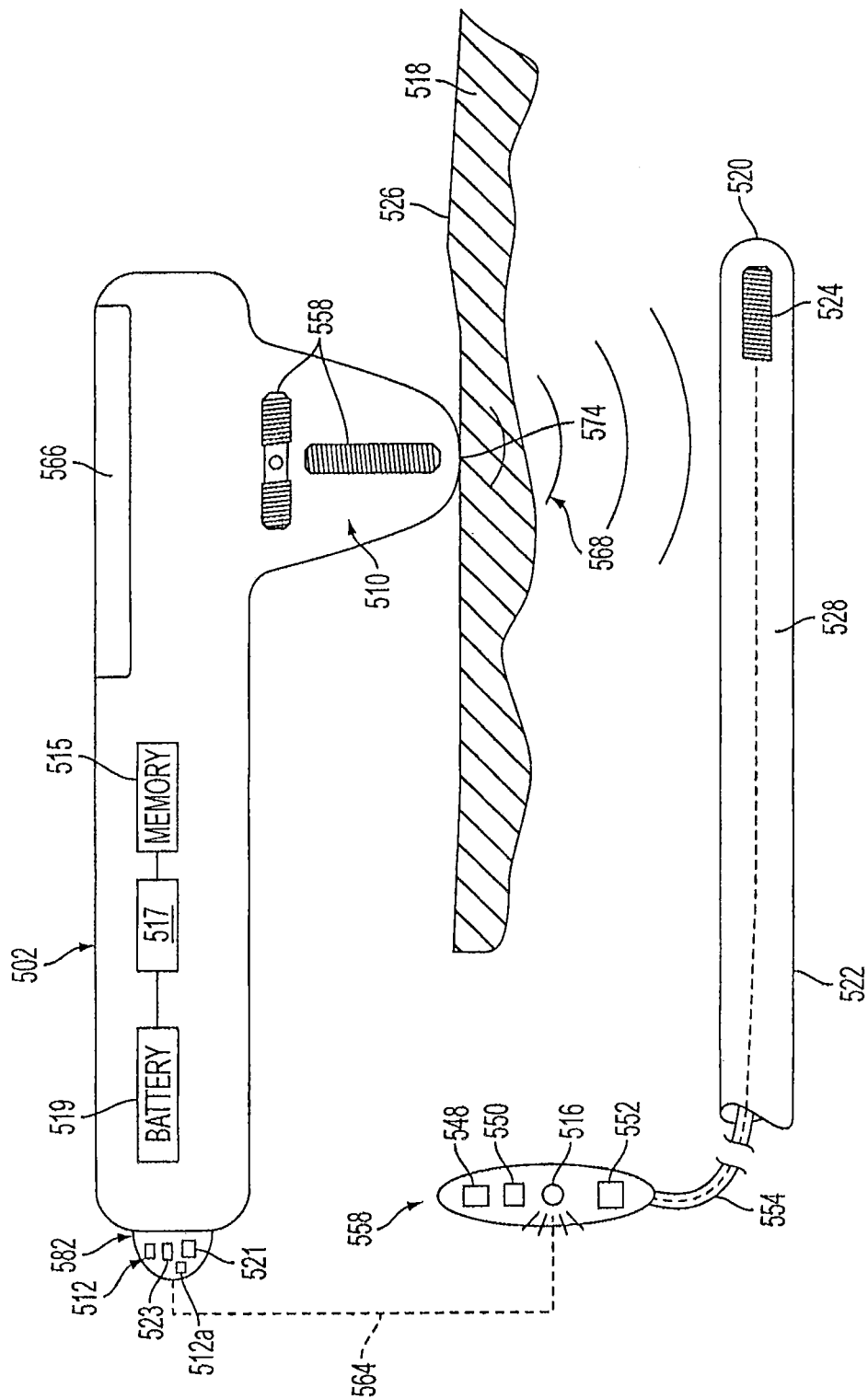
FIG. 3 is an elevated side and schematic view of an embodiment of a catheter assembly communicating with the noninvasive device, where the noninvasive device uses a vertically-oriented output coil.

In an embodiment of the medical device position guidance system 500, the magnetic field generator 510 includes a plurality of electromagnetic output coils 558, as illustrated in FIG. 3. As illustrated in FIG. 1, the user inserts a predetermined length of the catheter assembly 504 into the patient's blood vessel 532. In one example, an outer wall of the catheter includes markings indicating the length of the catheter 522 that has been inserted.

The user or medical personnel moves the noninvasive device 502 over the skin 518 of the human body 506 and powers-on the magnetic field generator 510 to generate a magnetic field. The user moves the noninvasive device 502 to direct the generated magnetic field through the skin 518 of the human body 506 to a location that is proximate to the estimated position of the end or tip 520 of the catheter 522. The receiver 512 receives radio wave signals from the transmitter 516 of the catheter assembly 504, as described in further detail below. In an embodiment, the receiver 512 includes an antenna 512a, as illustrated in FIG. 1, to receive radio frequency signals and is connected to a processor 523 that is powered by a battery 521.

Figure 2:
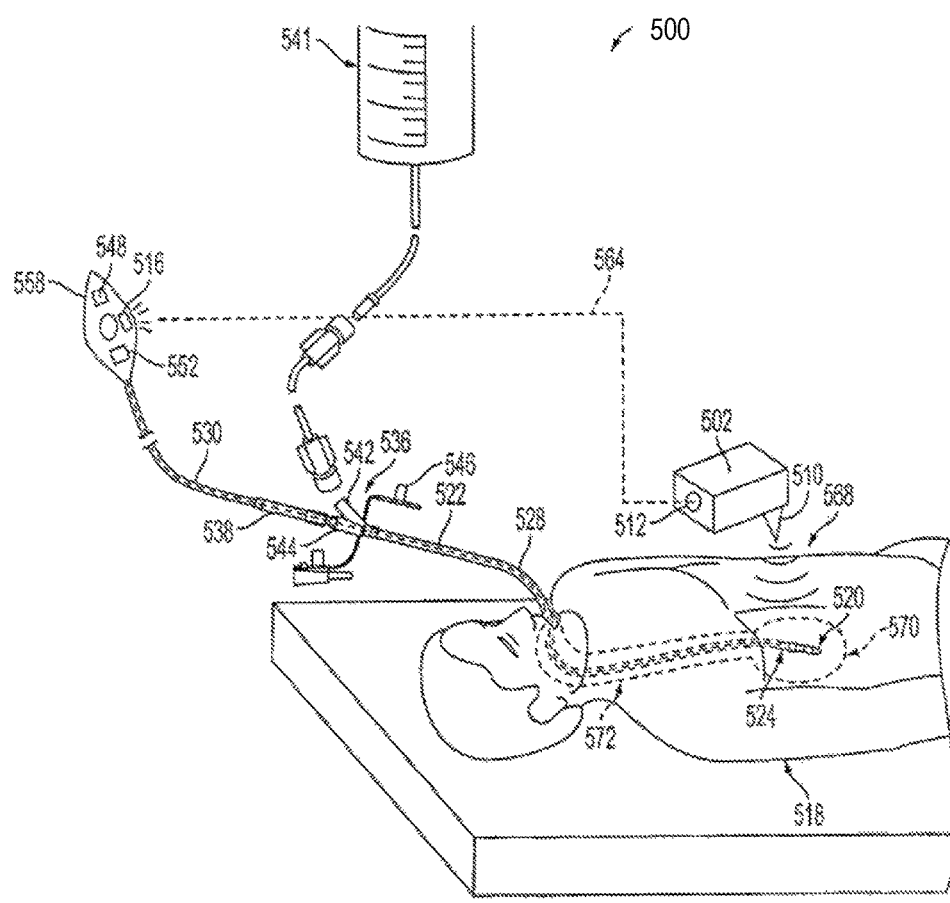
FIG. 2 is a perspective view of the medical device position guidance system illustrating an enteral application involving a catheter inserted into a human body and illustrating communication between the catheter assembly and the noninvasive device.
Figure 13:
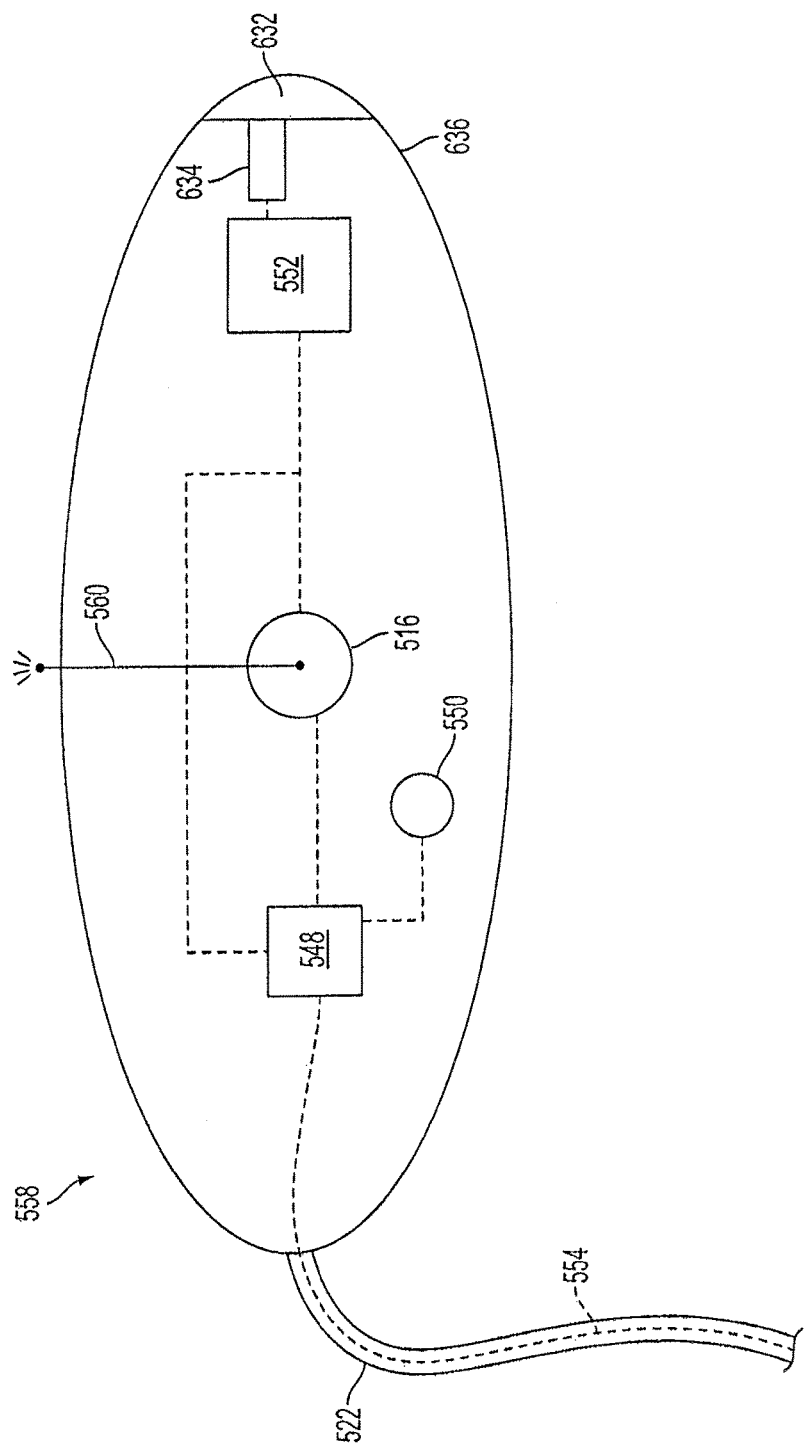
FIG. 13 is an enlarged top, schematic view of the noninvasive portion of the catheter assembly.

In an embodiment, the catheter assembly 504 includes a catheter 522 that is sized and shaped to be inserted into an animal. A distal end 528 of the catheter 522 may be inserted intravenously as shown in FIG. 1 into a vein, artery or blood vessel 532 of the human body 506 or enterally as shown in FIG. 2 into the gastrointestinal tract. In one example illustrated in FIG. 1, the user or medical personnel inserts the distal end 528 of the catheter 522 through the arm vein 532 to a position adjacent to the heart 534 of the body 506 of a patient. In an embodiment, the catheter assembly 504 includes a y-port connector 536. Branched end 542 of the y-port connector 536 connects, directly or indirectly, to a fluid source 540. The fluid source 540 may be medicine or any other suitable fluid used in intravenous or intravascular medical procedures. It should be appreciated that the branched end 542 of the y-port connector 536 may be closed off by an end cap 546 depending upon the medical procedure that is implemented. The branched end 544 of the y-port connector 536 is matably connectable through connector 538 to the extension 530 of the catheter 522. Referring to FIG. 1, the extension 530 of the catheter 522 includes a noninvasive portion carrying an antenna 560, as shown in FIG. 13, a processor 548, one or more indicators 550 and a battery 552. The battery 552 supplies power to the indicator 550, the processor 548 and the antenna 560. The catheter assembly 504 also includes an elongated conductor 554 connected to the processor 548 which runs through the extension 530 of the catheter 522, through the connector 538, through the y-port assembly 536, and continues to a coil 524 at the distal end 528 of the catheter.

In one embodiment, a stylet is operatively connected to the transmitter 516 and includes a tube and a guidewire supported inside the tube. The guidewire includes a steering wire or core wire and an elongated conductor wire. In an embodiment, the steering wire or core wire has a stiffness characteristic to facilitate with steering of the tip of the tube through a passageway in an animal. In an embodiment, the conductor wire is a single wire having a positive end and a negative end, which are positioned adjacent to each other at the proximate end of the core wire. Along the length of the core wire, the ends of the conductor wire are twisted about the core wire to shield or reduce any magnetic fields generated by the conductor wire along the length of the core wire. At the distal end of the core wire, the conductor wire forms a helical coil configured to induce a current when exposed to a magnetic field. In an embodiment, the core wire also functions as a grounding device for the antenna 560 of the transmitter 516, as shown in FIG. 13. Therefore, the antenna's ground device includes the core wire. In other embodiments, a suitable grounding device is incorporated directly into the antenna.

In another embodiment, the conductor 554 includes at least one conductor wire 554a axially twisted about a relatively stiff guidewire, and these wires function as a stylet, aiding the user in steering the catheter 522 inside the human 506. The coil 524 is, in one embodiment, comprised of a helical structure formed by multiple spirals of the distal end 528 of the conductor wire 554a. However, it should be appreciated that, in other embodiments, the coil 524 can be a separate wire coil unit which is operatively coupled to the conductor 554 in any suitable fashion. It should also be appreciated that, in another embodiment, the antenna 560, processor 548 and battery 552 can be housed, lodged or otherwise incorporated into the walls of the distal end 528 of the catheter 522.

Referring to FIG. 1, in one embodiment, when the connector 538 is disconnected from the y-port assembly 536, the conductor 554 and the coil 524 can be withdrawn through the distal end 528 of the catheter 522 out of the vessel 532 of the patient while the catheter 522 remains inside the patient. In an example, the user removes the conductor 554 and sensor coil 524 from the body after the medical device position guidance system 500 assesses the actual or approximate position and orientation of the tip or end 520 of the catheter 522 in the patient. In this example, after the wire 554 and sensor coil 524 are withdrawn, fluid can be introduced from the fluid source 540 or other medical treatment can be performed at the treatment site inside the vessel 532.

In operation, in an embodiment, as shown in FIG. 1, the user or medical personnel: (a) inserts a catheter a known or approximate distance into the vessel 532 of the patient; (b) activates the noninvasive device 502 to begin generating the magnetic field; (c) moves the noninvasive device 502 to direct the generated magnetic field 568 as shown in FIG. 3 in the proximity of where the tip 520 of the catheter 522 is estimated to be located; (d) receives an indication from the noninvasive device 502 regarding the relative position and orientation of the catheter tip 520 with respect to the noninvasive device 502; and (e) adjusts the position of the noninvasive device 502 or the catheter assembly 504 or both until the user is comfortable with the location of the catheter tip 520 within the vessel 532.

In an embodiment, the noninvasive device 502 includes a main battery 556 that provides a voltage to the plurality of electromagnetic output coils 558, as illustrated in FIG. 3, to produce the magnetic field. Referring to FIGS. 1 and 3, the magnetic field propagates through the tissue or skin 518 of the patient 506 and induces a voltage in the coil 524. The induced voltage travels through the wire 554 to the processor 548 of the transmitter assembly 558. The processor 548 of the transmitter assembly 558 converts the induced voltage and supplies information to the transmitter 516. The transmitter 516 wirelessly outputs the information through an antenna 560 as illustrated FIG. 13 in the form of modulated electromagnetic waves or radio waves. In one example, the frequency of the radio waves is approximately seventy hertz. However, it should be appreciated that the frequency may be any suitable frequency to allow radio communication between the transmitter and the receiver.

Figure 5:
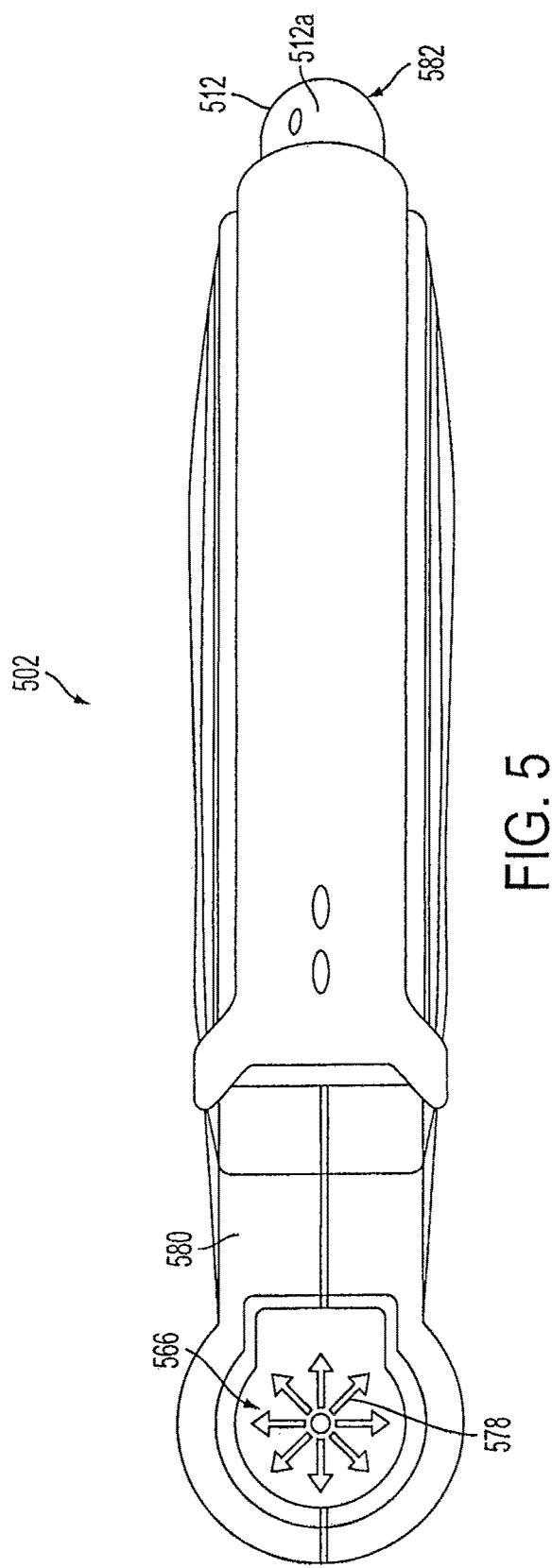
FIG. 5 is a top view of the noninvasive device, according to an embodiment.

As illustrated in FIG. 1, the radio waves wirelessly travel through the communication channel 564 or atmosphere to an antenna 512a of the receiver 512 of the noninvasive device 502. In an embodiment, the transmitter assembly 558 also includes one or more indicators 550 that indicate, upon instruction from the processor 552, whether the information has been successfully transmitted. However, the indicators 550 may also be used to indicate other operating parameters such as battery 552 strength, for example. The induced voltage in the coil 524 provides information regarding the proximity of the tip 520 of the catheter 522 to the noninvasive device 502 over the surface of the human. The induced voltage also provides information regarding the directional orientation of the tip 520 of the catheter 522 relative to the noninvasive device 504. The receiving processor 523, as illustrated in FIG. 3, receives information, transmitted by the transmitter 516 of the transmitter assembly 558, and the receiver processor 523 converts this information from a sinusoidal electromagnetic wave having a determined modulated frequency to a series of electrical impulses. The receiver processor 523 sends these impulses to the main processor 517 through one or more pins within the receiver 512. The main processor 517, as directed by the instructions of memory device 515, processes these impulses to cause the indicator 566 of the noninvasive device as illustrated in FIG. 5 to provide visual output in the form of the selection illumination of the directional arrow light sources 578. The arrow lights 578 indicate whether the tip 520 is pointed North, East, South, West or in between such directions. The main processor 517 also causes a speaker 586 to generate a series of variable tones. The main processor 517 varies the series of tones by frequency, volume or pitch to indicate whether the user is moving the noninvasive device 502 closer to, or further away from, the tip 520 in the human body. It should be appreciated that, the indicators 566 can include one or more light emitting diodes (LEDs) or display devices, such as liquid crystal display (LCD) panels operable to provide graphics and images related to the position of the tip 520.

The noninvasive device 502 is operatively connectable to, and in communication with, the catheter assembly 504 wirelessly through the two antennas 516 and 512. Therefore, in this embodiment, the noninvasive device 502, has no lead wires or cables physically connecting the noninvasive device 502 to the catheter assembly 504. As such, the noninvasive device 502 can be fully contained within a disposable sterile bag or envelope to protect the patient from contamination that may arise with respect to cross-patient uses of the noninvasive device 502. Accordingly, the noninvasive device 502 may be reused over a series of procedures with different patients while facilitating sterility. Also, the lack of wires attached to the exterior of the noninvasive device 502 minimizes or reduces the possibility of wires becoming tangled with the medical personnel or other equipment during a medical procedure.

Figure 4:
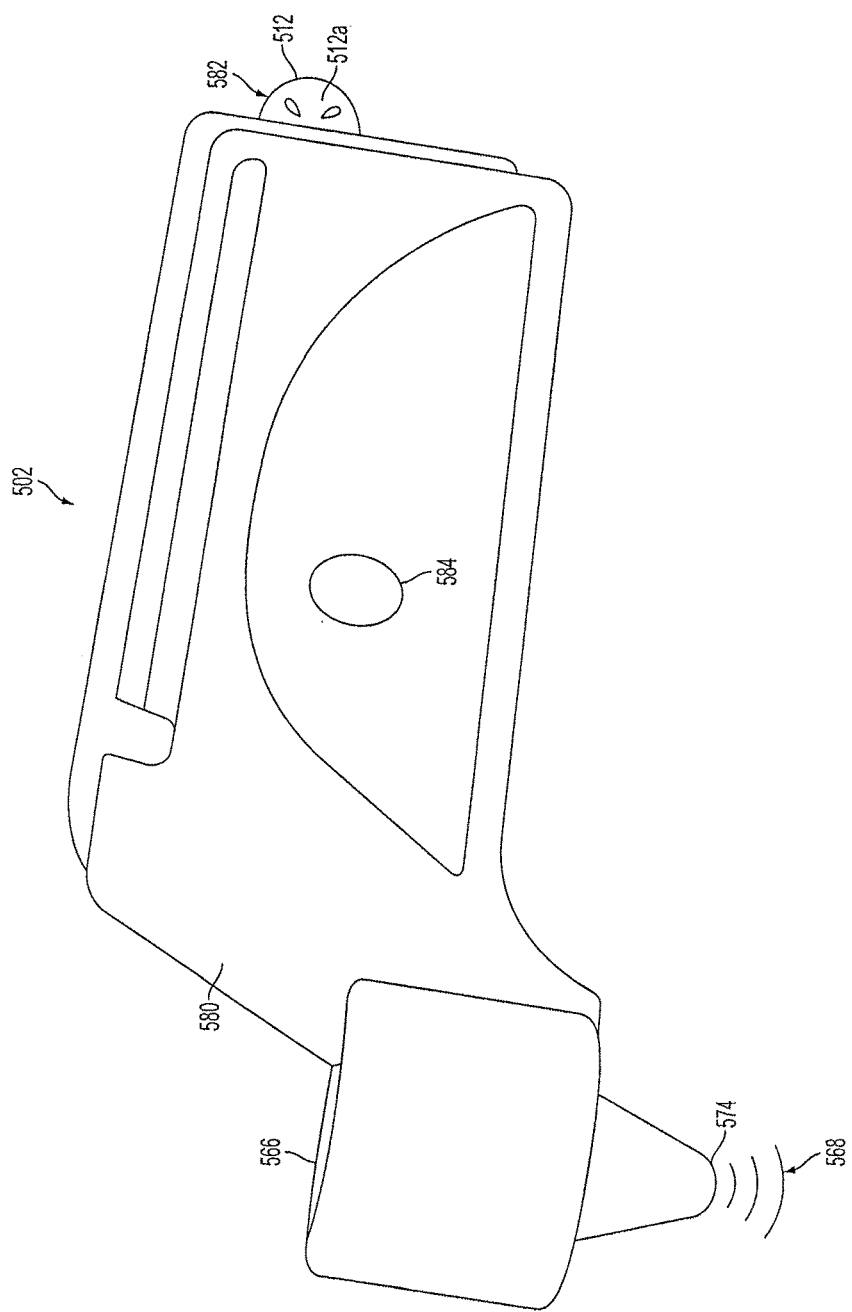
FIG. 4 is a perspective view of the noninvasive device, according to an embodiment.
Figure 6:
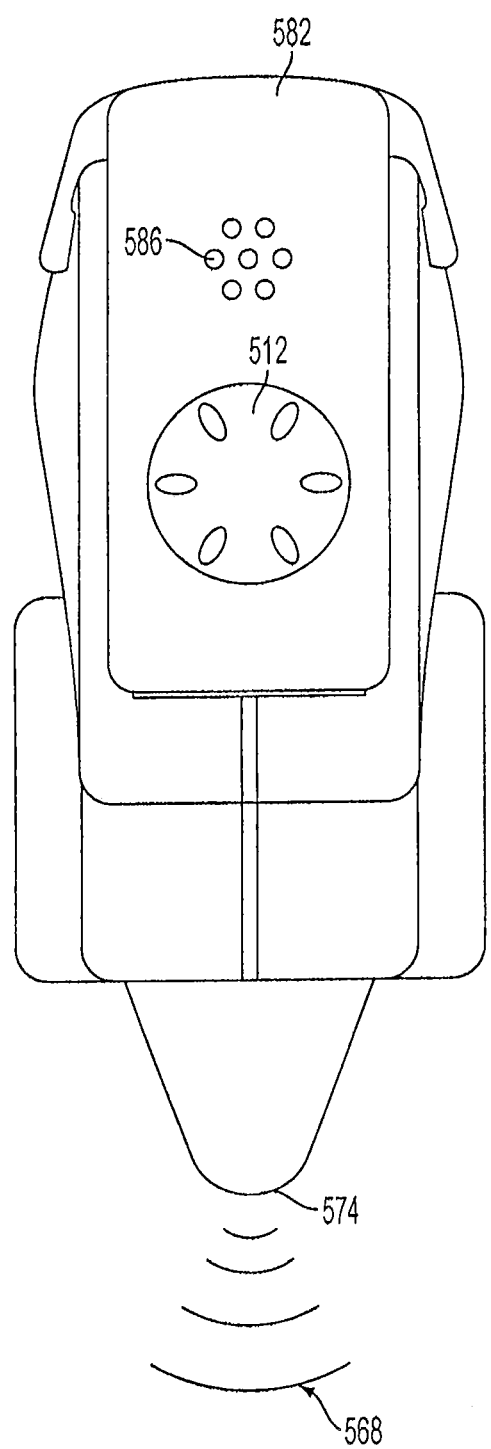
FIG. 6 is a rear view of the noninvasive device, according to an embodiment.

In an embodiment, with reference to FIGS. 4 to 6, the receiver 512 of the noninvasive device 502 is attachable to the main housing 580 of the noninvasive device 502 as a removable modular unit 582. In an embodiment, this modular unit 582 includes a dedicated battery 521 as shown in FIG. 3, and one or more electrical connections to removably connect to corresponding electrical connections located on the main housing 580. For example, the electrical connections may be a multiple pin and socket arrangement. In this embodiment, the processor 523 converts the modulated radio waves received through the antenna 560, as shown in FIG. 13 into electrical impulses, and the electrical impulses are transmitted through the electrical connectors. The electrical impulses are interpreted by a the main processor 517 housed in the main housing 580, as illustrated in FIGS. 3 and 4. The main processor 517 controls the indicators 566 based on this information. The noninvasive device 502 includes a power switch 584, illustrated in FIG. 4, that activates the battery in the main housing 580 to provide power to the main processor 517 and indicators 566 of the noninvasive device. In the embodiment where the modular unit 582 has a secondary battery or power source, the power switch 584 may also activate the secondary battery. However, it should be appreciated that the modular unit 582 may also include a separate power switch to activate the secondary battery.

In one embodiment, the modular unit 582 has a plurality of internal walls configured to mate with walls of the main housing 580 in a press-fit connection. By removing or attaching the unit 582, the user can convert the noninvasive device 502 between: (a) wireless communication mode in which the device 502 communicates with the catheter assembly 504 through antenna 516 and 512 and (b) a mode in which the device 502 is physically connected to the catheter assembly 504 through a data cable.

Referring to FIG. 13, in an embodiment, the transmitter assembly 558 includes a battery 552, a processor 548, an indicator 550, and a transmitter 516. The transmitter assembly 558 also includes a rotatable plug or cap 632 that is operable to electrically connect the battery 552 to the processor 548. In one embodiment, the rotatable cap 632 includes a threaded connector that can be screwed onto a portion of the noninvasive housing 508 and has an electrical contact that is movable between: (i) a first position in which the battery 552 is electrically disconnected from the processor 548; and (ii) a second position in which the battery 552 is electrically connected to the processor 548. In one example, the battery 552 is initially in a non-activated state before the catheter assembly 522 has been used and the user screws on the rotatable cap 632 to an end portion 636 of the transmitter assembly 558 to engage the contact 634 with an electrical contact of the processor 548 to allow the battery to provide power to the processor 548, the indicator 550 and the transmitter 516. As mentioned above, the transmitter 516 converts the electrical impulses sent through the wire 554 into modulated radio waves and emits the radio waves out through the antenna 560. In other embodiments, the electrical contact 634 may be a removable insulating film or other suitable device operable to cause the battery circuit to close when the film is removed from the circuit.

With certain invasive medical procedures, it is desirable to dispose of and incinerate the catheter assembly 504 because portions of the catheter assembly 504 have contacted bodily fluids such as blood or gastrointestinal fluids. It is often desirable to dispose of the battery 552 rather than attempting to incinerate the battery 552. In one embodiment, the battery 552 is housed in the rotatable cap 632 which can rotate in the opposite direction or be unscrewed to completely remove the battery 552 and the rotatable cap 632 from the catheter assembly 504. In this embodiment, the rotatable cap 632 facilitates disposal of the battery separate from the catheter assembly.

Figure 14A:
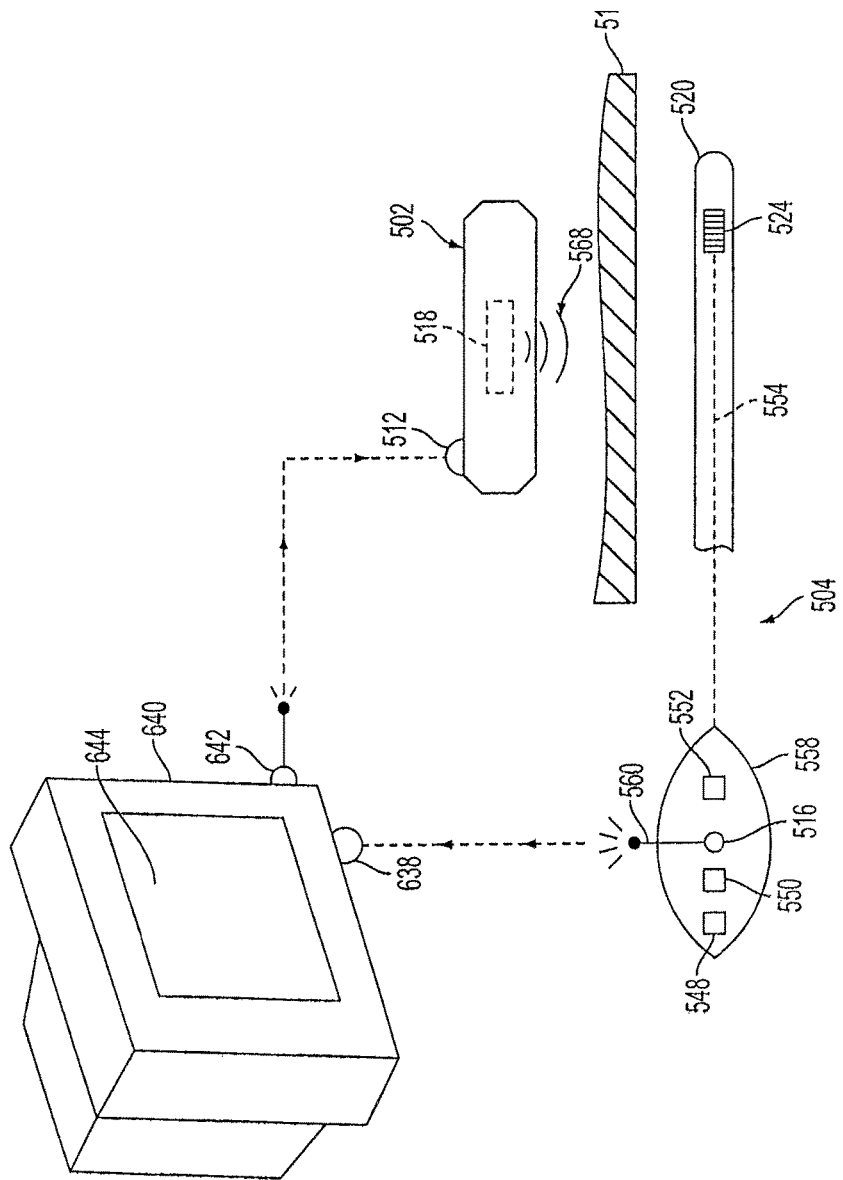
FIG. 14A is a schematic view of the medical device position guidance system illustrating an embodiment where the invasive device and the noninvasive device communicate indirectly with one another through a main processing unit.

Referring to FIG. 14A, in an embodiment, the transmitter 516 of catheter assembly 504 is configured to communicate indirectly with the receiver 512 of the noninvasive device 502. In one example, the transmitter 516 transmits radio waves through antenna 560 to a receiver 638 of a central processing unit 640. The receiver 638 of the central processing unit 640 converts the modulated radio waves into electrical impulses that are supplied to the processor of the central processing unit 640. In an example, the central processing unit 640 is a computer having a processor and a display device 644. In this embodiment, the display device 644 displays information regarding the position and orientation of the medical device in the body of the patient relative to the noninvasive device 502. The central processing unit 640 also includes a transmitter 642 to communicate with the receiver 512 of the noninvasive device 502.

Figure 14B:
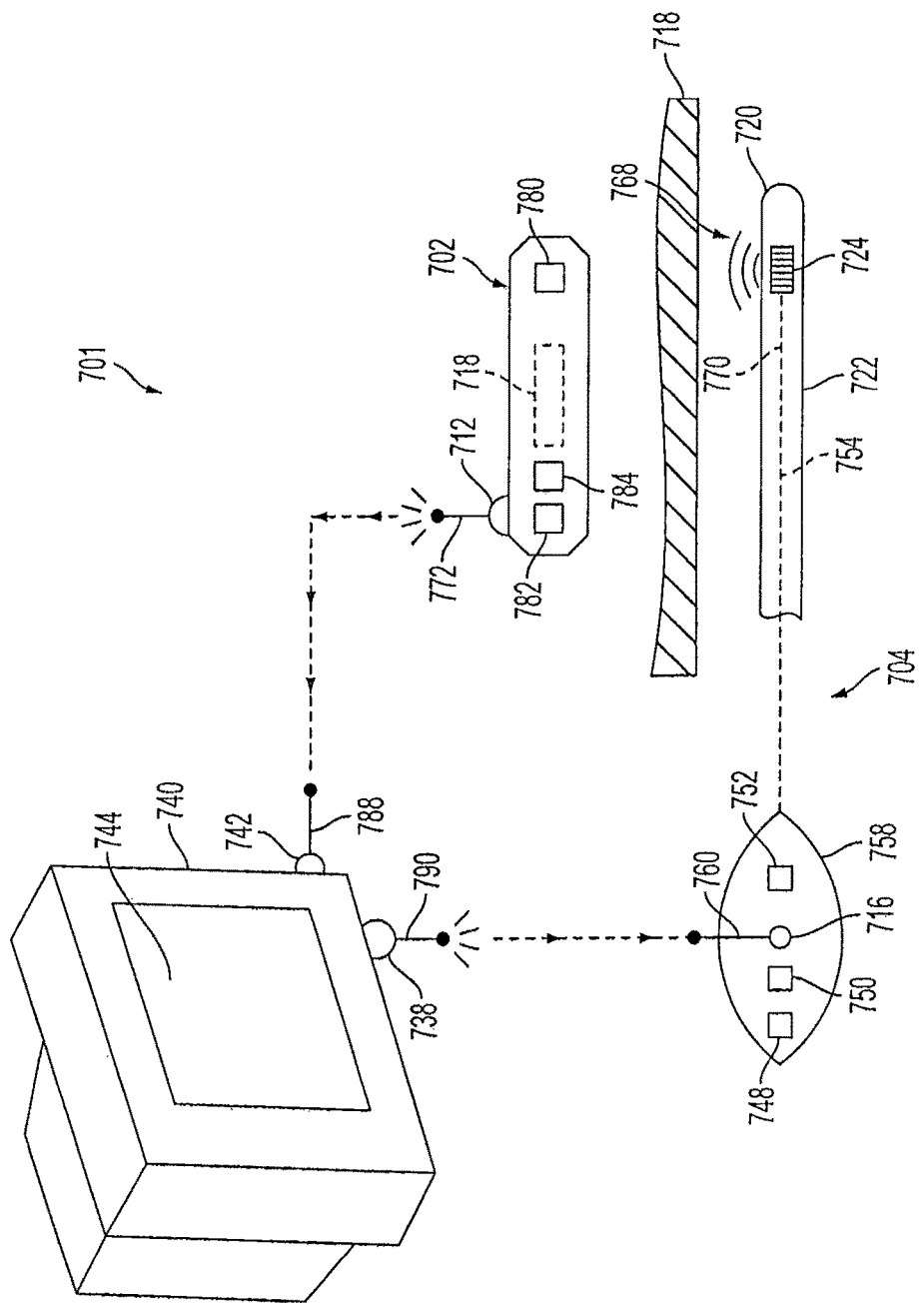
FIG. 14B is a schematic view of the medical device position guidance system illustrating an embodiment where the invasive device and the noninvasive device communicate indirectly with one another through a main processing unit.

Referring to FIG. 14B, in an embodiment, medical device position guidance system 701 includes a noninvasive device 702 and a medical device 704. In this embodiment, the medical device 704 is configured to communicate indirectly with the noninvasive device 702 through a central processing unit 744. As shown in FIG. 14B, medical device 704 includes: (a) a catheter 722 having an invasive end or tip 720; (b) a receiver housing 758 that houses a receiver 716 having an antenna 760, a battery 748, a processor 750, and an indicator 752; (c) a conductor 754 supported by the catheter 722 and operatively connected to the receiver 716; and (d) an invasive magnetic field generator 724 operatively connected to an invasive distal end 770 of the conductor 724 and powered by the battery 748.

The noninvasive device 702 includes: (a) a transmitter or transceiver 712 having an antenna 772; (b) a battery 780; (c) a processor 782; (d) an indicator 784; and (e) one or more coils 710 operatively connected to the transmitter 712 through the processor 774. The coils are operable to receive an induced current in response to a magnetic field 768 generated by the magnetic field generator 724 when the magnetic field 768 is directed toward and reaches the coils 710. It should be appreciated that the coils 710 may be any suitable structure or structures capable of receiving a current in response to a generated magnetic field. The central processing unit 740 includes a display 744, a transceiver or receiver 742 having an antenna 788 and a transmitter or transceiver 738 having an antenna 790. It should be appreciated that although the transmitter 738 and receiver 742 are illustrated to be separate components, they may be the same component functioning as a transceiver and sharing an antenna.

In one embodiment, referring to FIG. 14B, in operation: (a) the central processing unit 740 causes the transmitter 738 to emit radio waves through the antenna 790; (b) the receiver 716 of the medical device 704 receives the radio waves through the antenna 760 and the processor 750 converts the radio waves to a series of electrical impulses; (c) the electrical impulses travel through the conductor 754 to the magnetic field generator 724; (d) the magnetic field generator 724 generates a magnetic field 768 that passes through the tissue 718 of the animal and induces a current in the coils 710 of the noninvasive device; (e) the processor 782 converts the induced current to radio waves that are emitted through the antenna 772 of the transmitter 712; and (f) the receiver 742 of the central processing unit 744 receives the radio waves through the antenna 788. In this embodiment, the display device 744 displays information regarding the position, path or shape of path, or orientation of the invasive portion of the medical device 704 in the body of the patient.

III. Enteral Application

Figure 7:
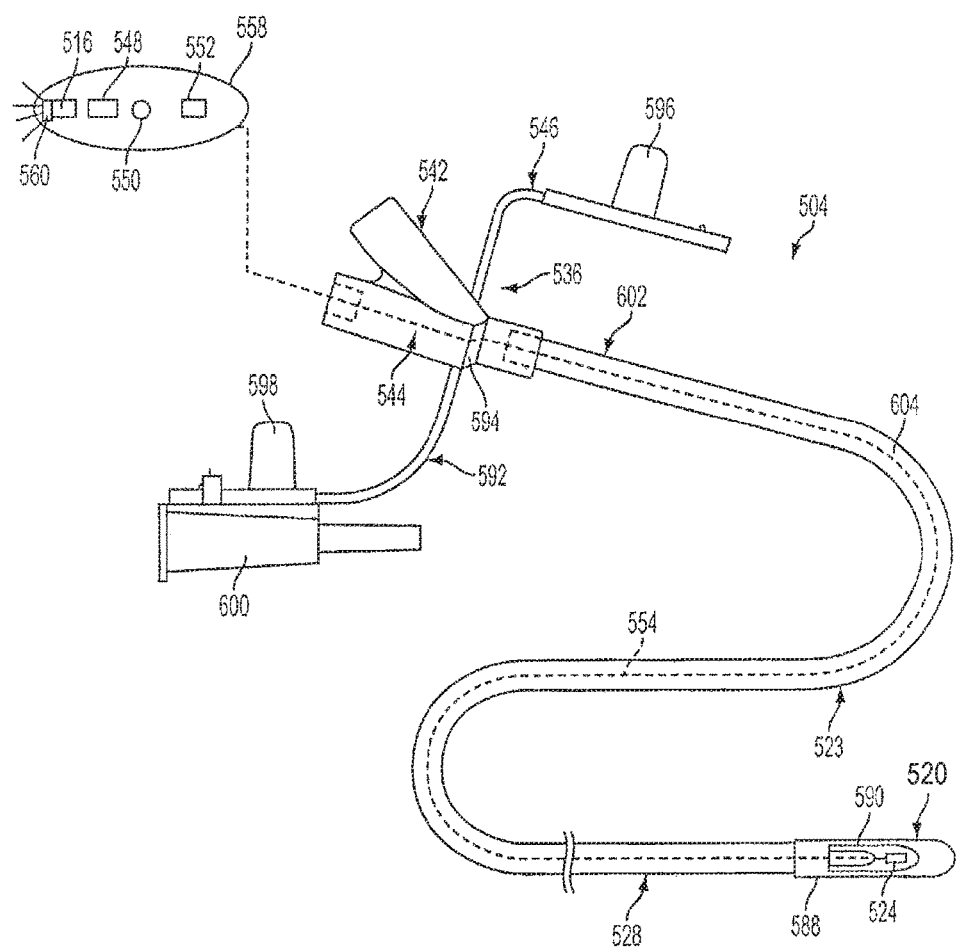
FIG. 7 is a top and schematic view of the enteral catheter assembly, according to an embodiment.
Figure 8:
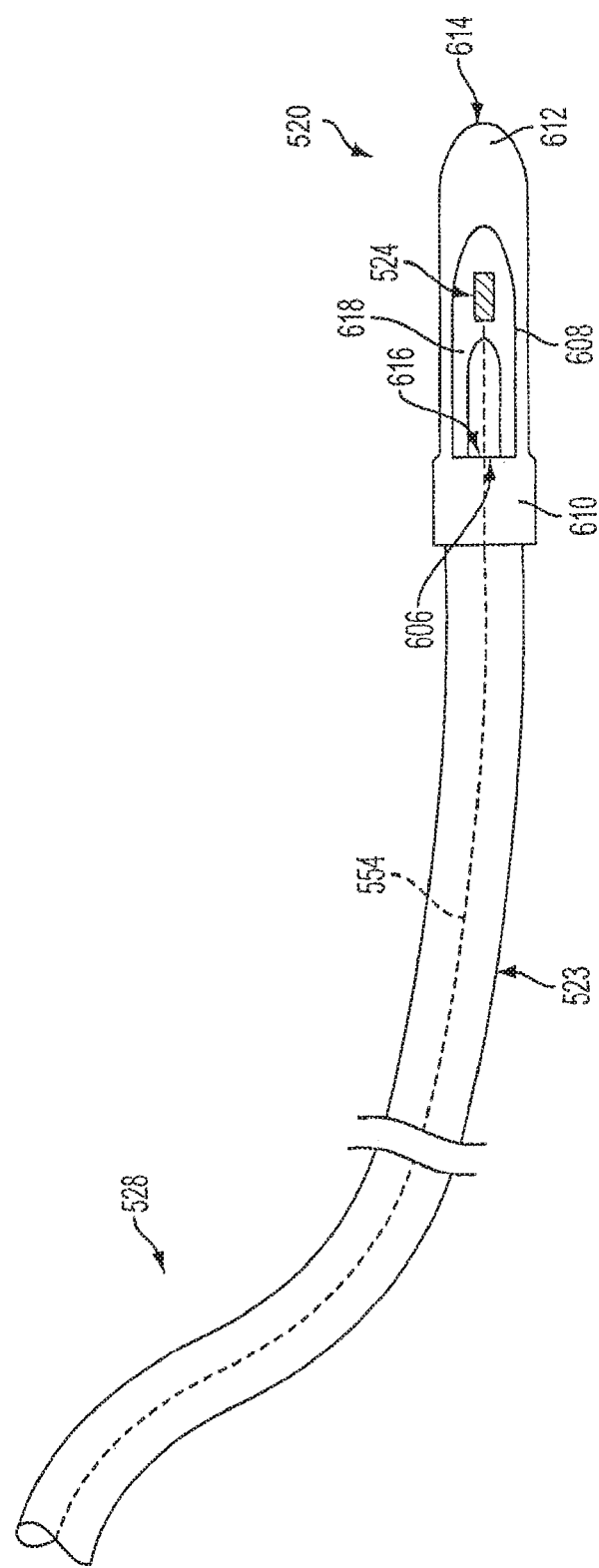
FIG. 8 is an enlarged top view of the enteral catheter illustrating the coil in the bolus of the catheter assembly of FIG. 7.

In an embodiment, as illustrated in FIG. 2, the medical device position guidance system 501 is utilized in an enteral application. Here, the system 501 includes the same components, elements, structure and functionality as system 500 except that system 501 includes enteral catheter 523 and enteral fluid source 541 instead intravascular catheter 522 and intravascular catheter 522 and intravascular fluid source 540, respectively. As illustrated in FIGS. 7 and 8, the enteral catheter 523 has a partially rounded end, tip 520 or bolus. The bolus has a plurality of lowered side walls which define an upper opening. In one embodiment, the bolus defines an additional opening at its end.

In this application, the user or medical personnel positions the noninvasive device 502 over the skin or tissue 518 of a patient. In this enteral application of the medical device position guidance system 501, the distal end 528 of the catheter 523 is inserted through the mouth and esophagus 572 into the enteral cavity 570 of a patient. The branched arm 542 of the y-port connector 536 connects to a fluid source 541 such as a feeding bag. The medical device position guidance system 501 provides the user with audio-visual information to assist in assessing the position of the end or tip 520 of the catheter 523 as described above with respect to the intravascular system 500. As such, the enteral system 501 reduces the risk that the catheter may be inadvertently misplaced. Accordingly, the risk of injury to the patient is reduced.

Referring to FIGS. 7-8, in one embodiment, the multi-port or y-port connector 536 includes: (a) a body 594; (b) a first branched arm or liquid delivery branch, medicine delivery branch or medicine branch 542 attached to the body 594 for distributing drugs, medicine or other medicinal liquids to the patient; (c) a second branched arm or catheter connection branch 544 attached to the catheter 522; (d) a flexible or movable arm 592 attached to the body 594; and (f) a flexible or moveable arm 546 attached to the body 594. In an alternative embodiment, y-port connector 536 includes additional branches for administering various nutrients or medicines to the body. In another alternative embodiment, the y-port connector 536 includes only a feeding branch 542 and a connection branch 544. The arm 546 has a stopper 596, and the arm 544 has a stopper 598. The stoppers 596 and 598 are sized to prevent fluid from passing through the branches 544 and 542 after such branches 544 and 542 are plugged with stoppers 596 and 596, respectively. In addition, the arm 544 includes a tube-size adapter 600 to the arm 544. The tube-size adapter 600 enables fluid delivery tubes (not shown) having various diameters to connect to the feeding branch 544 of the y-port connector 536.

As illustrated in FIGS. 7-8, in one embodiment, the enteral catheter 523 includes a feeding tube having: (a) a proximal end 602 attached to the catheter connection branch 544 of the y-port connector 536; (b) a distal end; and (c) an external surface 604. The proximal end 602 is insertable into the catheter connection branch 544 of the y-port connector 536 so as to bring the enteral catheter 523 into fluidic communication with the y-port connector 536. In one embodiment, the external surface 604 has a plurality of volumetric, measurement or unit markings (not shown) uniformly spaced along enteral catheter 523. These markings assist the user in measuring the flow or distribution of liquid to or from the patient. In an alternative embodiment, markings function as placement markers which assist the user in assessing the depth that the catheter is placed within the human body. In this embodiment, the markings may be used to make the initial estimation as to where the tip 520 or end of the catheter 523 is within the patient or body. Then the medical device positioning guidance system 500 is used to provide audiovisual information about the position of the tip 520.

As best illustrated in FIG. 7, in one embodiment, the conductor 554 connects to the coil 524 and runs through the catheter 522, through the first branched arm 544 of the y-port connector 536 and on to the transmitter assembly 558. As described above, the electrical impulses induced in the coil 524 are sent along the wire and converted by the transmitter 516 into modulated radio waves.

As best illustrated in FIG. 8, in one embodiment, the end member, bolus or tip 520 is attached to the distal end 606 of the catheter 522. As described above, the tip 520 includes a body 608 having a collar 610 and an end member 612. The body 608 defines a passage 616 and an opening 618. The opening 618 is positioned between the collar 610 and the end member 612. A portion 614 of the end member 612 can have a rounded shape. The shape of the passage 616 and opening 618 of the tip 520 is configured to facilitate the flow of fluid from the catheter 522 into the patient's body while decreasing the likelihood that the opening 618 will become clogged.

IV. Other Applications

Figure 9:
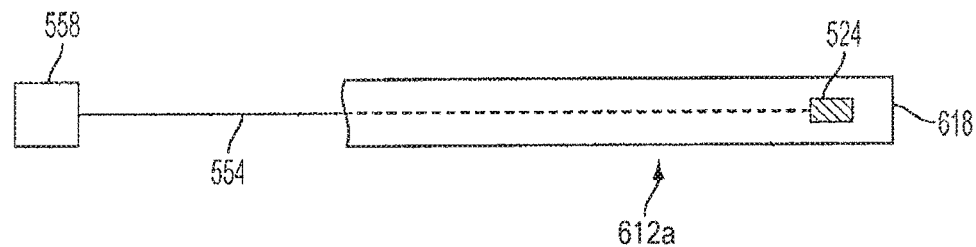
FIG. 9 is a schematic view of a catheter assembly having a catheter with an open end.
Figure 10:
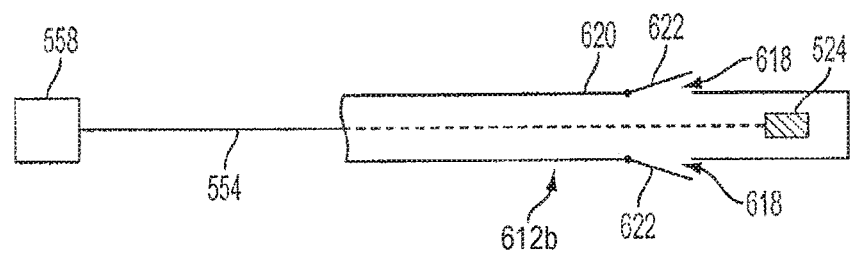
FIG. 10 is a schematic view of a catheter assembly having a catheter with flapped openings on the sidewalls of the catheter.

It should be appreciated that the noninvasive device 502 and transmitter assembly 558 can be used together in a variety of medical applications. In one embodiment, as illustrated in FIG. 9, the transmitter assembly 558 is coupled to a catheter with an opening 618 located on the portion 614 of the end member 612. In this embodiment, the end member 612a is tubular and may be cut such that the opening 618 is circular and defined by the tube diameter. In another embodiment, as illustrated in FIG. 10, the transmitter assembly 558 is coupled to a catheter that defines one or more openings 618 located on a sidewall 620 of the end member 612b. In this embodiment, the sidewall 620 is cut to form flaps 622 that allow fluid to be dispensed to the patient.

Figure 11:
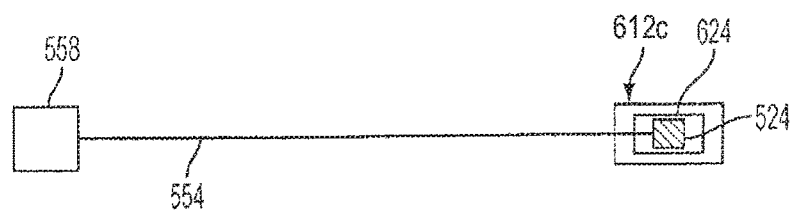
FIG. 11 is a schematic view of a catheter assembly having a medical treatment device disposed at an end of the catheter for use in ablation therapy or other types of medical treatment.

In another embodiment, as illustrated in FIG. 11, the transmitter assembly 558 is coupled to an end member 612c through a wire 554. In this embodiment, the end member includes a medical device 624 such as a radio frequency or thermal energy ablation device. In one example, the medical device 624 does not include a catheter, and thus, it not configured to deliver fluid to the patient. In this embodiment, the coil 524 transmits electrical impulses through the wire 554 to the transmitter assembly 558, as discussed above.

Figure 12:
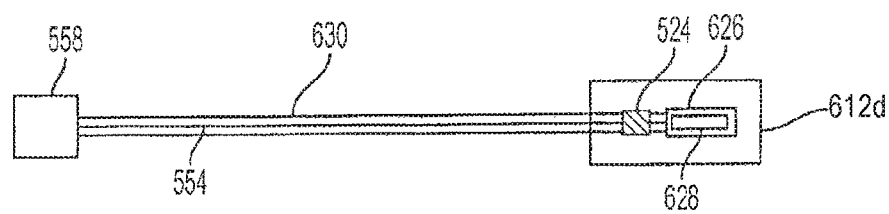
FIG. 12 is a schematic view of a catheter assembly having a stent and a balloon at an end of the catheter for use in stenting operations.

In one embodiment, as illustrated in FIG. 12, the transmitter assembly 558 is coupled to the end member 612d through a wire 554, as discussed above. In this embodiment, the end member 612d includes a stent 624 and a balloon 626 inserted within the stent. In operation, the medical device position guidance system 500 facilitates locating the position of the coil 524 and the stent 626 within the body, as discussed above. After the location of the stent 626 is assessed, an operator or medical personnel inflates the balloon 628 by pumping a gas through an air passageway 630 such as a tube. The inflation of the 628 deploys the stent 626 within a vein or artery of the patient. The balloon 628 is then deflated and balloon 628, coil 524, wire 554, and air passageway 630 are withdrawn from the vein or artery of the patient.

Although the above embodiments relate to positioning an end of a catheter, an ablation therapy device and a stent, it should be appreciated that the medical device position guidance system 500 is operable to assist the placement of any medical device or invasive component into an animal in the course of stent placement, ablation, blockage removal, heat treatment, surgical procedure, fluid delivery or any other suitable invasive procedure. It should be appreciated that any type of catheter may be used for any of the medical procedures described above. It should also be appreciated that any suitable invasive medical device can be used in place of a catheter.

V. Electronic Configuration for Magnetic Sensing

Referring to FIGS. 15 to 25, in an embodiment, the noninvasive device 502 and catheter assemblies 522 and 523 include the components, elements, structure and functionality described above in addition to the components, elements, structure and functionality of the system 10 described below. System 10 is used for externally locating a sensor in tissue. The sensor is typically an inductive coil placed within a catheter near its tip. The system 10 also includes an external, noninvasive device which generates electromagnetic fields which penetrate the patient's skin and couple to the sensor coil. The induced sensor coil voltages are detected. The sensor coil voltages, and the drive signals used to create the electromagnetic fields in the noninvasive device, are compared, to assess the distance between the noninvasive device and the sensor coil, the relative angular orientation, in a horizontal plane, between the catheter and the noninvasive device, and to assess when the noninvasive device is directly over, or very close to, a plane bisecting the center of the sensor coil. The user thus is able to assess the location of the catheter tip, the depth of the catheter in the body, and the direction in which the catheter tip is pointing. This allows the user to confirm that the catheter tip is in the correct location, and pointing in the correct direction, to assist in proper catheter placement.

Figure 15:
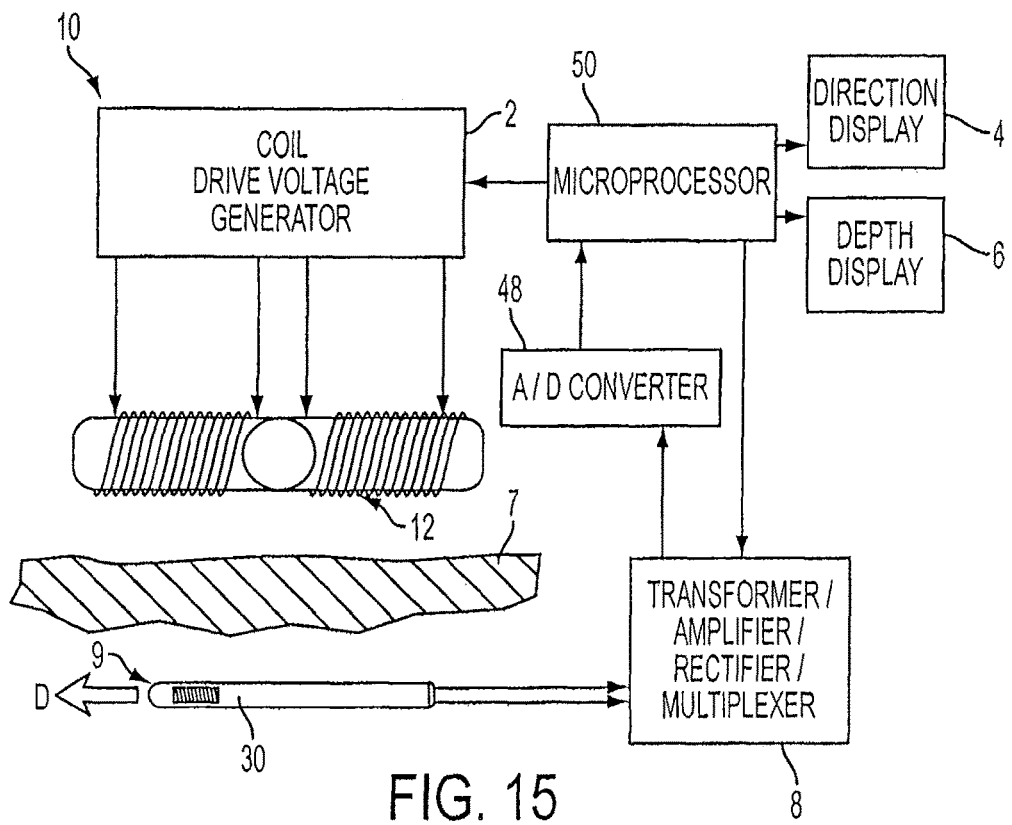
FIG. 15 is a simplified schematic block diagram of one embodiment of a catheter locating system.

There is shown in FIG. 15, system 10 according to this embodiment for externally locating a sensor placed in a patient's body. System 10 includes an noninvasive device which includes pair 12 of perpendicular electromagnetic output coils. Coil pair 12 is moved over skin 7 to detect the depth of, and angular orientation of, inductive sensor coil 30 carried by and proximate the distal end of catheter 9 located under skin 7.

The coils of coil pair 12 are driven by high frequency signals developed by coil drive voltage generator 2 under control of microprocessor 50. The coil drive voltages are preferably time-multiplexed to allow a single frequency source in microprocessor 50 to be used to generate the drive signals for both coils.

The electromagnetic fields generated from coil pair 12 penetrate skin 7 and induce voltages in sensor coil 30. These induced signals are transformed, amplified, rectified and multiplexed by transformer/amplifier/rectifier/multiplexer circuit 8. A transformer is used to isolate the patient from the input amplifier circuitry. The analog output signal of circuit 8 is then digitized by analog-to-digital (A/D) converter 48. The digitized signals are provided to microprocessor 50, which assesses from these signals, and the drive signals provided to coil drive voltage generator 2, both the distance between coil set 12 and sensor coil 30, and the direction D (called the "true direction") in which the distal end of catheter 9 is pointing. The depth is displayed to the operator by depth display 6. The catheter true direction is displayed to the operator by direction display 4.

Figure 16A:
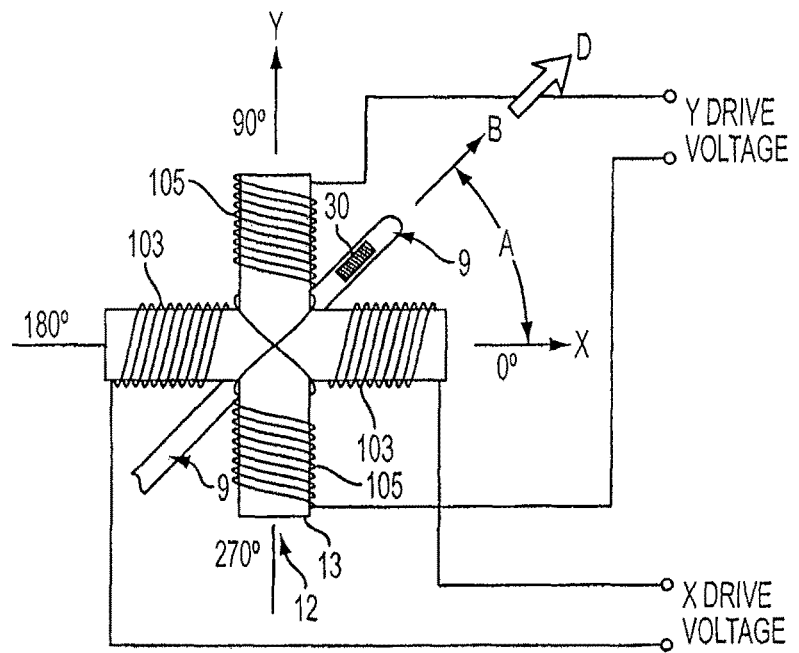
FIG. 16A is a schematic diagram of the pair of horizontal field generating coils located over the catheter of the system of FIG. 15, useful in illustrating the catheter depth determination accomplished by the system of this embodiment.

A form of coil pair 12 is shown in more detail in FIG. 16A. Coil pair 12 includes cross-shaped coil form 13 on which are wound perpendicular, coplanar coils 103 and 105. Form 13 may be magnetic material or not. In the drawing of FIG. 16A, the longitudinal axis of coil 103 lies along an X-axis, and the longitudinal axis of coil 105 lies along a Y-axis. For convenience of reference hereinafter, coil 103 will on occasion be referred to as "the X coil," while coil 105 will on occasion be referred to as "the Y coil." Coil set 12 is shown as being almost directly above sensor coil 30 of catheter 9. Longitudinal axis X of coil 103 is non-parallel to longitudinal axis Y of coil 105. Preferably, the axes are perpendicular. Longitudinal axis B of sensor coil 30 lies at an angle A from axis X. The direction of the arrowhead on axis B also indicates the direction in which the distal end of catheter 9 is pointing (the true direction).

Coils 103 and 105 are driven separately by an X drive voltage and Y drive voltage, respectively, generated by coil drive voltage generator 2, FIG. 15. Together, coil drive voltage generator 2 and microprocessor 50 shown in FIG. 15 alternately energize coils 103 and 105. The distance determinator shown in FIG. 15 includes transformer/amplifier/rectifier/multiplexer 8, A/D converter 48, and microprocessor 50 which together assess from the voltage induced in sensor coil 30 the distance between sensor coil 30 and coils 103 and 105. Preferably, all of the components of system 10, with the exception of catheter 9, are carried by an noninvasive device (not shown).

Coils 103 and 105 are alternately energized to generate a time-varying magnetic field which penetrates a patient's skin. In one embodiment, the time-varying magnetic field is created by first driving X coil 103, and then driving Y coil 105 with the same high frequency voltage. Coils 103 and 105 are then again sequentially driven by the same voltage, but reversed in phase in relation to the voltage used to drive the coils the first time. This scheme creates a magnetic field whose axis points in sequence to 0°, 90°, 180° and then 270°. This pattern is repeated over and over to create a virtual rotating magnetic field. In another embodiment, which is the embodiment which is employed in the remainder of the description of the embodiments, coils 103 and 105 are driven alternately by the same drive voltage, without the phase reversal discussed above. This creates a magnetic field whose axis points in sequence to 0°, 90°, 0°, 90°, etc.

Because coils 103 and 105 are driven alternately without phase reversal, the voltage induced in coil 30 is related to both the sensor-to-coil distance, as well as the horizontal angle A of sensor axis B relative to X-coil 103 axis X, and Y-coil 105 axis Y. If Vsx is defined as the voltage induced in sensor coil 30 by the field from coil 103, and Vsy the coil 30 induced voltage from coil 105, those values may be determined by the following equations:

where
Vsx=induced sensor voltage due to field from X coil
Vsy=induced sensor voltage due to field from Y coil
k=a constant
A=horizontal angle between the projection of the axis of the sensor coil and the projection of the axis of the X coil into a plane parallel to the X and Y coils' axes
d=distance between sensor and output coils Vsx is thus a maximum when A=0°, and a minimum when A=90°. Conversely, Vsy is maximum when A=90°, and minimum when A=0°. The vector sum of Vsx and Vsy, is independent of angle A. If this vector sum is labeled Vsh, the following holds true:

Since $Vsh^2$ is in itself a quantity independent of angle A, it is not necessary to calculate the square root of the sum of the squares, as is done in equation (3). By not performing the square root calculation, the number of calculations required by microprocessor 50, FIG. 15, is reduced, allowing more time for other calculations to be performed by microprocessor 50.

Microprocessor 50 reads and stores the amplified, rectified Vsx and Vsy voltages, and performs the calculations of equations 1 through 3 to develop Vsh or $Vsh^2$. As explained below, microprocessor 50 then puts out digital information to drive depth display 6.

Figure 16B:
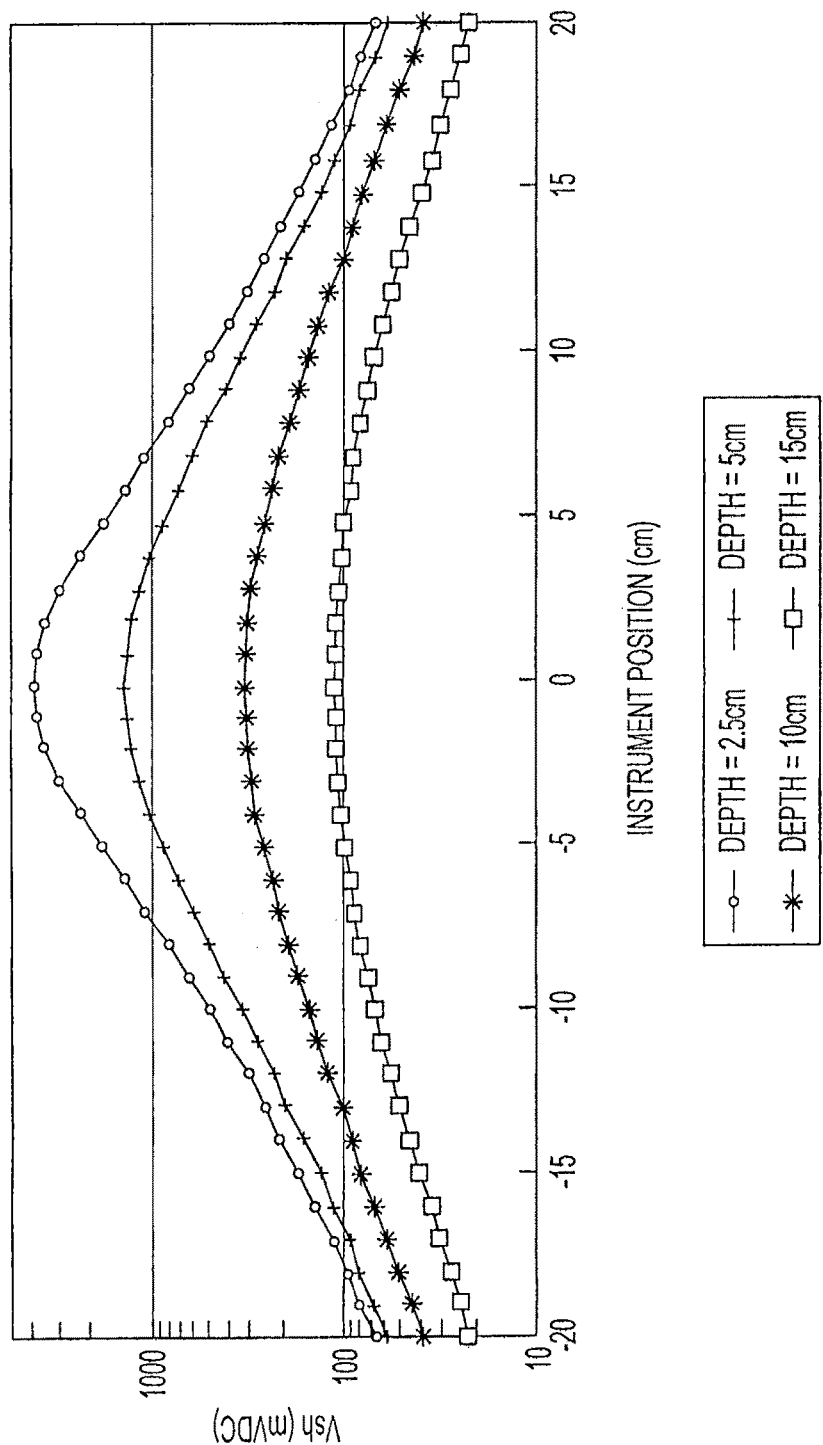
FIG. 16B is a graph of sensor coil voltage induced by the pair of horizontal field generating coils of FIGS. 15 and 16A at four different catheter depths as the horizontal field generating coils are moved horizontally along the patient's skin.

FIG. 16B is a graph of instrument position versus Vsh. Note that the voltage values on the vertical axis are logarithmic. Shown are measurements taken at sensor coil depths below coil pair 12 of 2.5 cm, 5 cm, 10 cm, and 15 cm. These appear from the top to the bottom of FIG. 16B in the order just listed. Coil pair 12 was moved at right angles to the sensor coil longitudinal axis, starting at a position directly over the sensor coil (0 cm), out to 20 cm in either direction from the sensor coil longitudinal axis. As can be seen, the drawing of FIG. 16B illustrates that the induced sensor voltage is maximum when the output coils are directly over the sensor coil. As the coil pair is moved horizontally in a straight line at right angles to the sensor coil axis, the sensor voltage decreases as shown.

Figure 17:
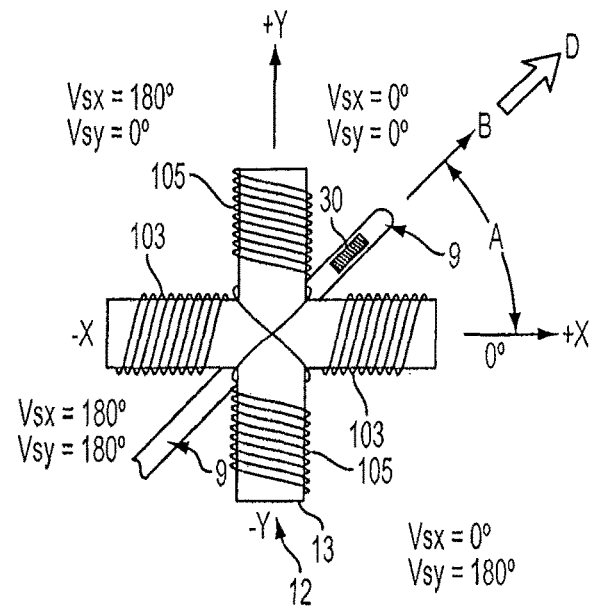
FIG. 17 is a view similar to that of FIG. 16A, illustrating the relative horizontal angular orientation of the sensor coil longitudinal axis, the longitudinal axes of the two horizontal field generating coils and the phases of the induced sensor voltages relative to the phases of the respective output coil drive voltages.

It is also desirable for the system of this embodiment to assess the true direction D in which the catheter tip is pointing. This is the direction of arrow B, FIG. 16A, which may be defined in relationship to the direction of axis X or axis Y. As shown in FIG. 17, the direction of sensor coil longitudinal axis B (the true direction) may be defined by angle A between axis B and axis X of coil 103. Microprocessor 50 calculates angle A according to the following equation:

where A is defined as the horizontal angle between sensor axis B and the X-coil axis X.

Angle A may lie in any one of the four quadrants defined by the X and Y axes. In order to assess the true direction in which the catheter tip is pointing, it is necessary not only to calculate the tangent of the angle A, but also to assess into which quadrant sensor coil 30 is pointing. This determination is made by measuring the phase between the voltage used to drive X coil 103, and the Vsx and Vsy voltages. When coil 30 is pointing to the positive X side of the Y axis, the phase difference between the X coil drive voltage and Vsx is 0 degrees. When output coil 30 is pointing to the negative X side of the Y axis, there is a 180° phase difference between those two voltages. Similarly, when sensor coil 30 is pointing to the positive Y side of the X axis, the Y coil drive voltage used to drive coil 105, and the voltage induced in the sensor coil from the Y coil voltage, are in phase (0 degrees). When sensor coil 30 is pointing to the minus Y side of the X axis, those two voltages are out of phase (180 degrees). Thus, by making the two phase comparisons, the quadrant is assessed, which then fully defines the direction of longitudinal axis B in relation to longitudinal axis X, thus determining the catheter distal end true direction.

Figure 18A:
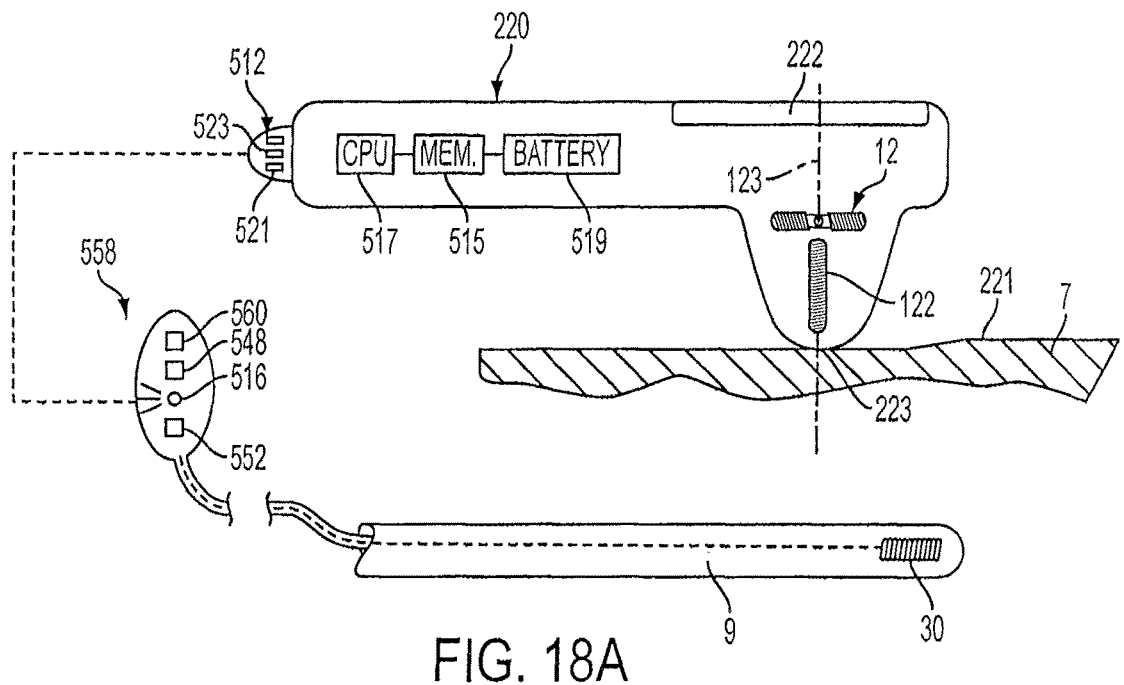
FIG. 18A is a cross sectional, schematic view of a catheter and one embodiment of the external noninvasive device of this invention that uses a vertically-oriented output coil.
Figure 18B:
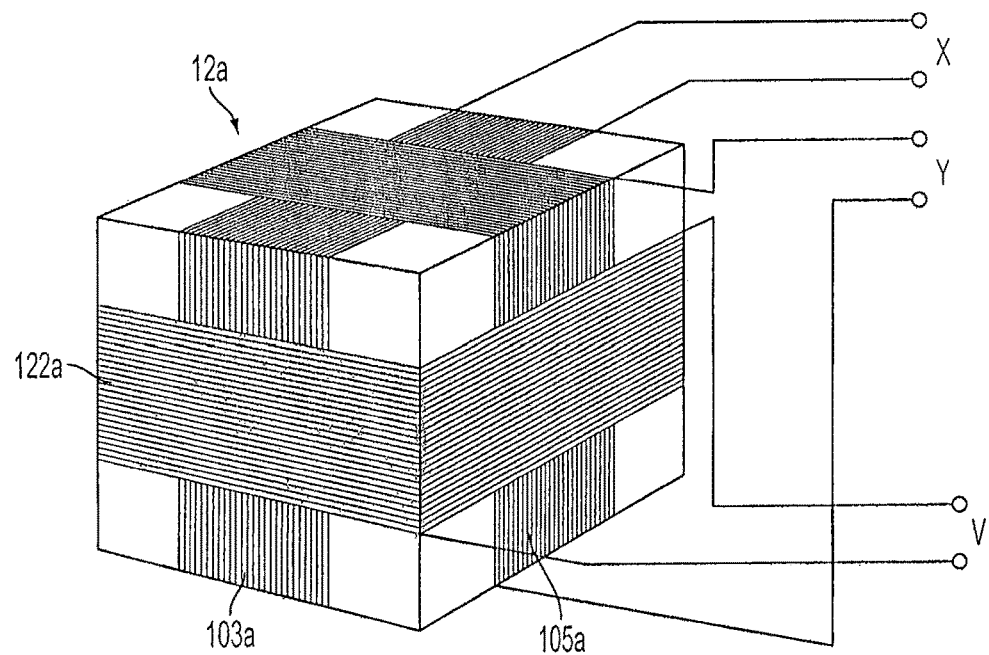
FIG. 18B is an alternate form of an output coil set incorporating a vertically-oriented output coil.

FIG. 18A is a cross sectional view through a embodiment of the noninvasive device 220 and the catheter 9 including sensor coil 30, of the system of this embodiment. FIG. 18A introduces an additional concept of a embodiment of the system of this embodiment. Noninvasive device 220 includes horizontal coil pair 12 as described above relative to FIGS. 16A and 17. Also included is vertically-oriented electromagnetic coil 122 which lies along "vertical" longitudinal axis 123, i.e., an axis transverse to a plane parallel to the axes of coils 103 and 105. FIG. 18B shows an alternate way of constructing coil set 12a to incorporate vertically oriented coil 122a and horizontal coils 103a and 105a. In use, noninvasive device 220 is held so that rounded noninvasive device tip 223 is on or next to the skin surface 221. As explained below, the noninvasive device is moved across surface 221 to locate sensor coil 30 near the distal end of catheter 9. As explained in detail above, the transmitter 516 wirelessly emits radio waves through antenna 560 which are then received by the receiver 512. The receiving processor 523, as illustrated in FIG. 18A, receives information, transmitted by the transmitter 516 of the transmitter assembly 558, and the receiver processor 523 converts this information from a sinusoidal electromagnetic wave having a determined modulated frequency to a series of electrical impulses. The receiver processor 523 send these impulses to the main processor 517 through one or more pins within the receiver 512. The main processor 517 processes these impulses to cause the indicator 566 of the noninvasive device as illustrated in FIG. 5 to provide visual output. Operator displays 222 mounted in noninvasive device 220 are described in more detail below.

Figure 19A:
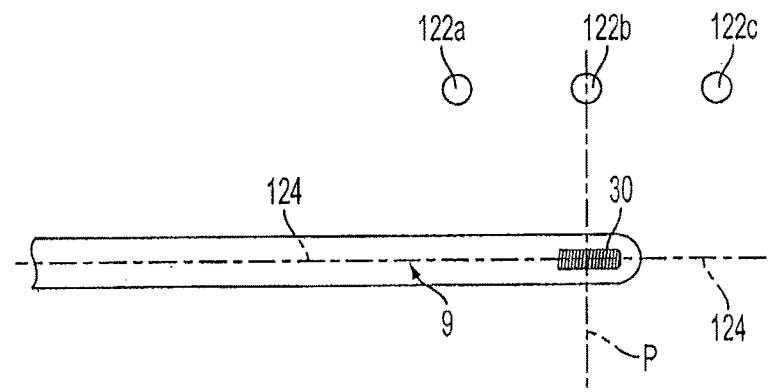
FIG. 19A is a view of the sensor showing an edge view of the plane which bisects the sensor midpoint.

Vertical coil 122, FIG. 18A, is used to assess when noninvasive device tip 223 is at or very close to plane P shown in FIG. 19A, which bisects sensor coil 30 and is perpendicular to longitudinal axis 124 of sensor coil 30. This embodiment of the system includes a sensor coil position determinator for determining, from the vertical output coil drive voltage, and the electrical voltage induced in sensor coil 30 by this vertical coil drive voltage, when the longitudinal axis 123 of vertical coil 122 is proximate plane P. This assesses more exactly the position of sensor coil 30 in relation to noninvasive device 220. This determination can be made in two ways. The first way is to measure the phase change of the induced sensor voltage.

As vertical coil 122 moves from one side of plane P to the other, the phase of the voltage induced in sensor coil 30, in relation to the phase of the high frequency drive signal used to drive coil 122, changes from 0° (in phase) to 180° (out of phase). For example, when coil 122 is at position 122a on one side of plane P, FIG. 19A, the two signals are in phase. When coil 122 is at position 122c on the other side of plane P, the signals are out of phase. When coil 122 is at position 122b, in which longitudinal axis 123 of coil 122 lies in plane P, there would be no signal. However, in reality the induced sensor signal in this case would very quickly alternate between being in phase and out of phase with the output coil drive signal, as due to movement of the operator's hand, and slight movements of the sensor coil in the patient, coil 122 would never actually remain exactly centered on plane P.

Figure 19B:
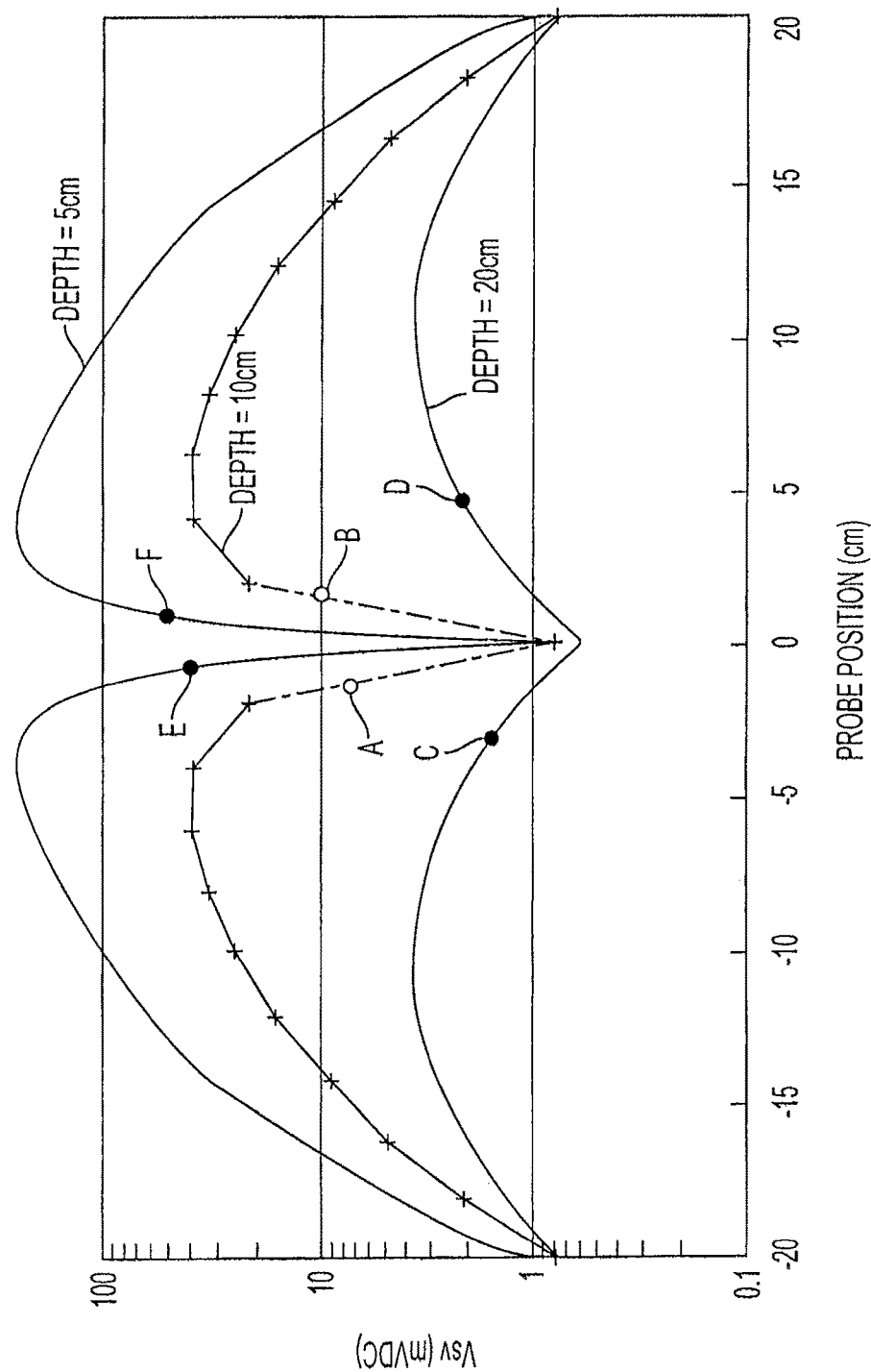
FIG. 19B is a graph of sensor coil output voltage induced by the vertical coil of FIG. 18A versus the distance of the vertical coil from the plane bisecting the sensor coil and perpendicular to the sensor coil longitudinal axis for three different sensor depths.

The second way to assess the position of sensor coil 30 in relation to noninvasive device 220 is to measure the change in amplitude of the induced sensor voltage. It has been found that the amplitude of the induced sensor voltage from the field generated from the vertical coil drops to a minimum, or a null, when the coil is directly over the plane P, (position 122b). As shown in FIG. 19B, the induced sensor voltage Vsv drops nearly to 0 when coil 122 is positioned in plane P. At a sensor coil depth of 10 cm, the voltage increases up to approximately 40 millivolts as the vertical coil is moved horizontally along axis 124, FIG. 19A, approximately 5 cm from plane P. Thus, the positioning of the vertical coil in relation to the sensor coil can also be assessed from the sensor coil output voltage. Detection of plane P may thus be based either on the phase change between the vertical coil drive voltage and the resulting induced sensor voltage, or by detection of the sensor voltage null. Null detection, the embodiment, is described in relation to FIGS. 20 through 23.

Figure 20:
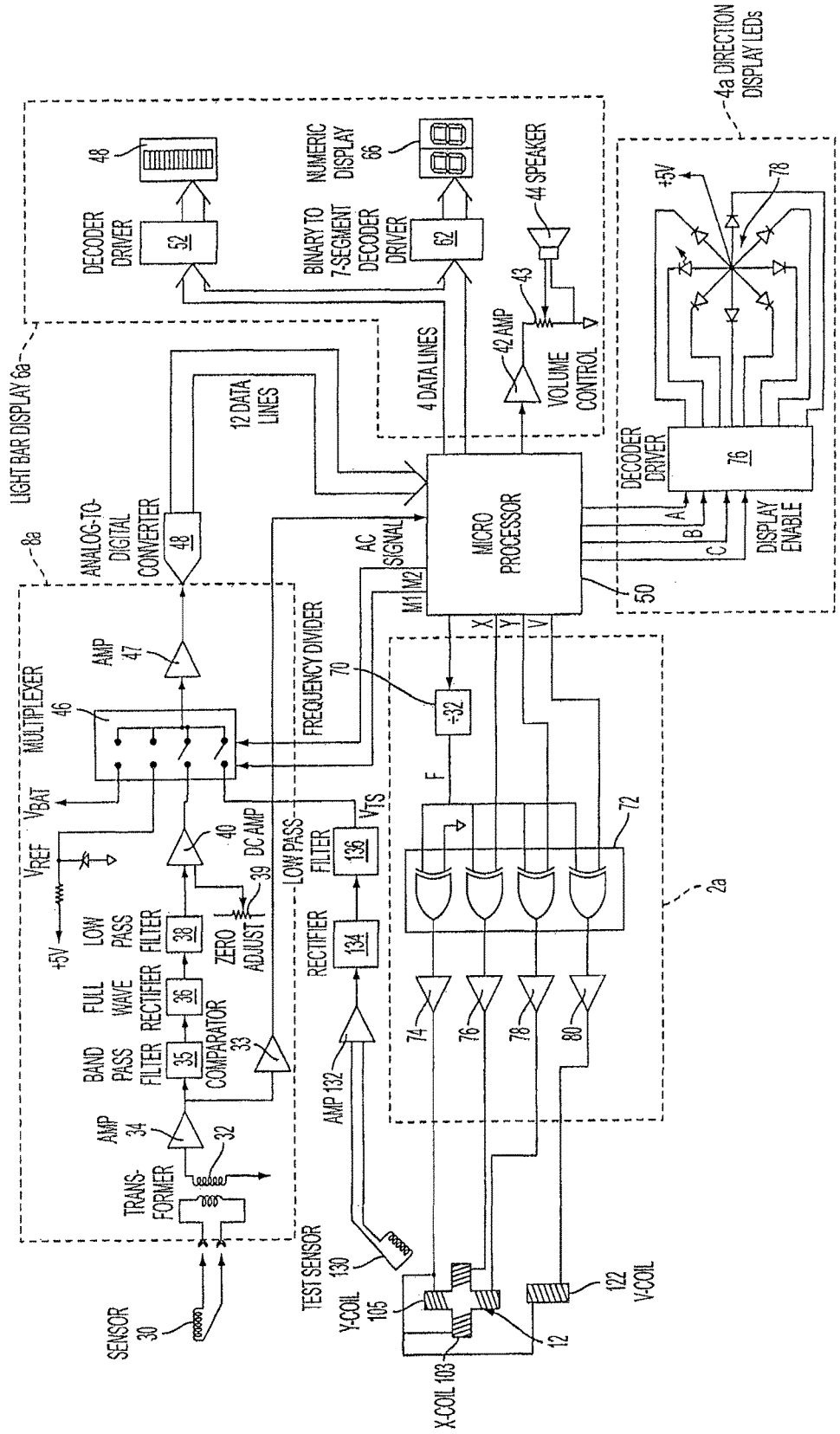
FIG. 20 is a schematic electronic diagram of the embodiment of the system of this invention.
Figure 21:
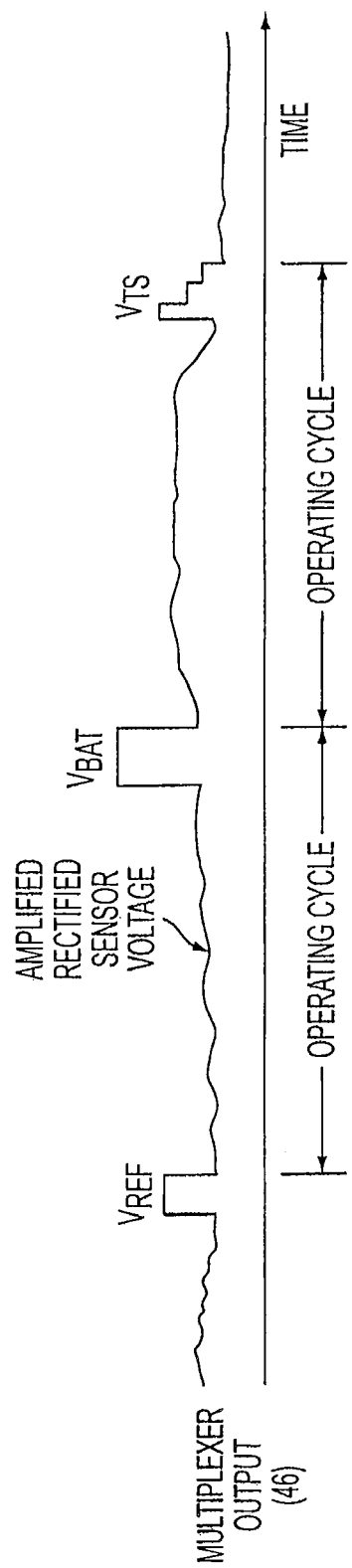
FIG. 21 is a timing diagram for the circuit of FIG. 20.

FIG. 20 is an electronic schematic diagram of the embodiment of the system of this embodiment. Horizontal output coils 103 and 105 are wound on cross shaped core 12. Also shown is vertically-oriented coil 122. The coils are driven sequentially as shown in FIG. 21. Signal F is a high frequency drive voltage derived by dividing the clock frequency of microprocessor 50 using frequency divider 70. In one embodiment, the microprocessor 50 clock frequency is 2 Mhz, and the divider ratio is 32, resulting in a frequency of signal F=62.5 kHz. The sequence of coil drives is established by the output coil driver means which includes microprocessor 50, frequency divider 70, exclusive OR circuit 72, and amplifiers 74, 76, 78 and 80. Microprocessor 50 also has control outputs labeled X, Y, and V, shown in FIG. 21. These control signals are provided to circuit 72 to result in multiplexed high frequency drive signals which are amplified and provided to the appropriate coil as the X coil, Y coil and V coil currents depicted in FIG. 21. The vertical coil is thus energized after each time that either the X coil or Y coil is energized. The resulting voltages induced in sensor coil 30 are also shown in FIG. 21. In this example, the sensor voltage induced by the X coil current is larger than that induced by the Y coil current. For other sensor coil directions, the sensor voltage induced by the X coil current may be smaller than or equal to that induced by the Y coil current.

The induced sensor voltage is coupled through isolation transformer 32 to amplifier 34, band pass filter 35, full wave rectifier 36, low pass filter 38, and DC amplifier 40. Zero adjustment 39 ensures that the output of amplifier 40 is 0 volts when the sensor is positioned remotely from all three of the output coils, at a point where virtually 0 voltage is induced in the sensor. The output of amplifier 40 is connected to multiplexer 46, whose timing is controlled by signals M1 and M2 from microprocessor 50. The multiplexing scheme is described below in conjunction with FIG. 23. The multiplexer output is connected to amplifier 47 which has a gain of 1. These components make up transformer/amplifier/rectifier/multiplexer circuit 8a. The rectified, filtered output signal of amplifier 40 is shown in the lowermost graph of FIG. 21.

Figure 22:
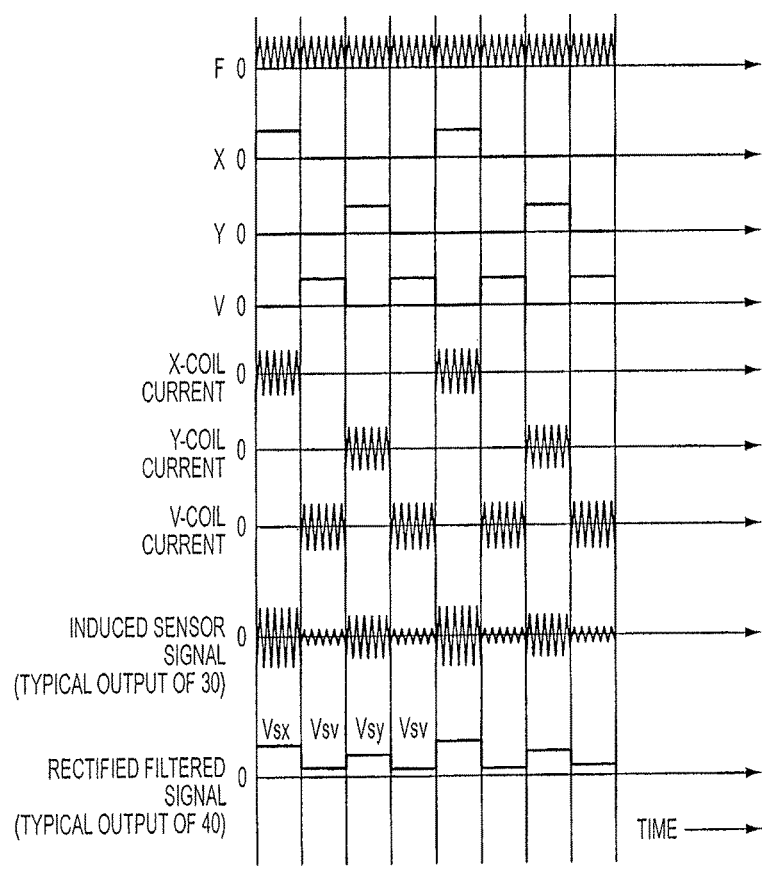
FIG. 22 depicts the multiplexer output for the system of FIG. 20, showing reference, battery, test sensor and sensor coil voltages.

As shown in FIG. 22, which is a graph of the output of multiplexer 46, the multiplexer is preferably timed to connect the amplifier 40 output voltage to amplifier 47 and then on to A/D converter 48 for the greater part of the measurement cycle. Multiplexer 46 is periodically connected to the battery voltage Vbat and precision DC voltage reference Vref, and to test sensor voltage Vts. In one embodiment, these three voltages are measured in sequence, once per second over three consecutive operating cycles. If the battery voltage Vbat drops below a predetermined threshold, microprocessor 50 is programmed to turn on a low battery indicator light. If the precision voltage reference Vref source changes value beyond a small tolerance, the microprocessor is preferably programmed to turn the instrument off.

Test sensor 130, FIG. 20, consists of a small inductive coil positioned adjacent to all three output coils. Typically, but not necessarily, its longitudinal axis is at a 45° angle to the longitudinal axes of all three output coils. The fields from each of the three output coils induce voltages in the test sensor which are amplified, rectified and filtered by amplifier 132, rectifier 134, and low pass filter 136, respectively. The resulting voltage Vts is periodically read by microprocessor 50. If an output coil should break, or if the coil drive current should fail or decrease beyond a preset limit, the test sensor output voltage Vts would change accordingly. The microprocessor is programmed to sense this and turn the instrument off such that the instrument is on only when functioning properly.

The digital output of A/D converter 48 is connected to microprocessor 50. Microprocessor 50 is programmed to store the three voltage levels Vsx, Vsy and Vsv and perform the appropriate calculations to assess the sensor depth (distance from output coils 103 and 105 to sensor coil 30) and the true direction determined from angle A, FIGS. 16A and 17, as described above. The calculated values are then displayed as outputs to the operator. The forms of the outputs are shown in FIG. 6 and also FIGS. 24A through 25.

Figure 24B:
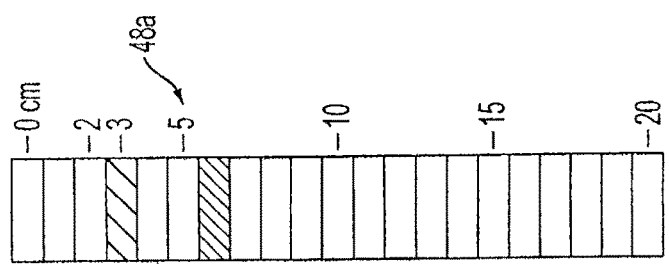
FIG. 24B is an enlarged view of the distance display of the noninvasive device of FIG. 24A.
Figure 24A:
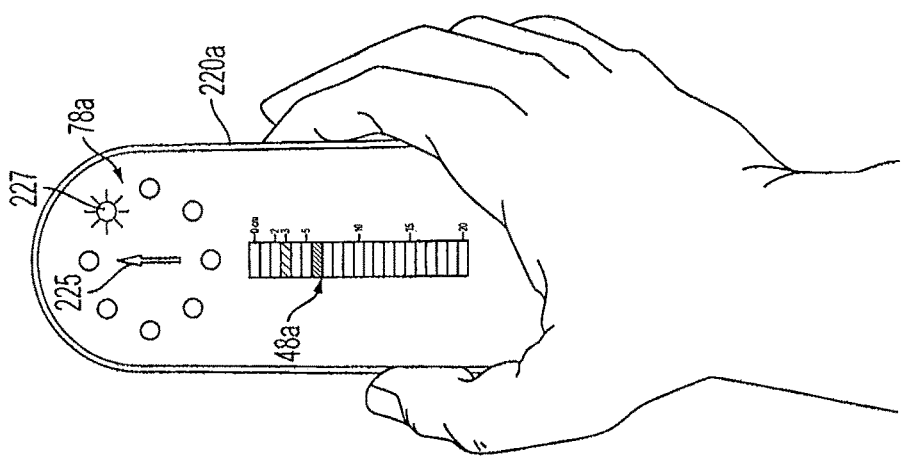
FIG. 24A is a top plan view of one form of an noninvasive device for the system of this invention.

Data establishing the sensor depth may be provided on four data lines to both decoder driver 52 and binary to seven-segment decoder driver 62. Driver 52 is enabled to drive light bar display 48, which may indicate the strength of the induced sensor voltage Vsh, shown in FIG. 16B. As illustrated in FIGS. 24A and 24B, light bar display 48a may be mounted on the upper surface of hand held noninvasive device 220a and include a number of segments which are typically LEDs with a scale of centimeters alongside. The minimum distance, which corresponds to the peak signal strength, is in one embodiment, continuously updated and the corresponding LED lit, along with the LED representing the currently-sensed distance, to give the operator a better idea of when the noninvasive device is closest to or directly over the sensor coil. Alternatively, numerical display 66, also shown as display 66a, FIG. 25, may be used to indicate the depth directly in inches or centimeters. The system converts Vsh (or $Vsh^2$) to distance by using the value of the variable to address a distance lookup table in microprocessor 50, FIG. 20. The lookup table stores numbers which convert to the depth (in inches, centimeters, or audio frequency).

Microprocessor 50 may also produce a variable frequency which is related to the induced sensor voltage and which is used to drive amplifier 42, which drives speaker 44 through volume control 43. This provides a tone whose frequency changes relative to the induced sensor voltage.

Direction display 78 in this embodiment consists of eight LEDs arranged in a circle as shown in FIG. 24A as direction display 78a. These LEDs are driven by decoder-driver 76, which converts digital information from microprocessor 50 to energize the appropriate direction-indicating LED such as LED 227, FIG. 24A. This direction display indicates that the distal end of the catheter is pointing in the direction of LED 227. This is the true direction in which the catheter distal end is pointing. This information is derived from the determination of angle A as described above in conjunction with FIGS. 24 and 27.

Figure 23:
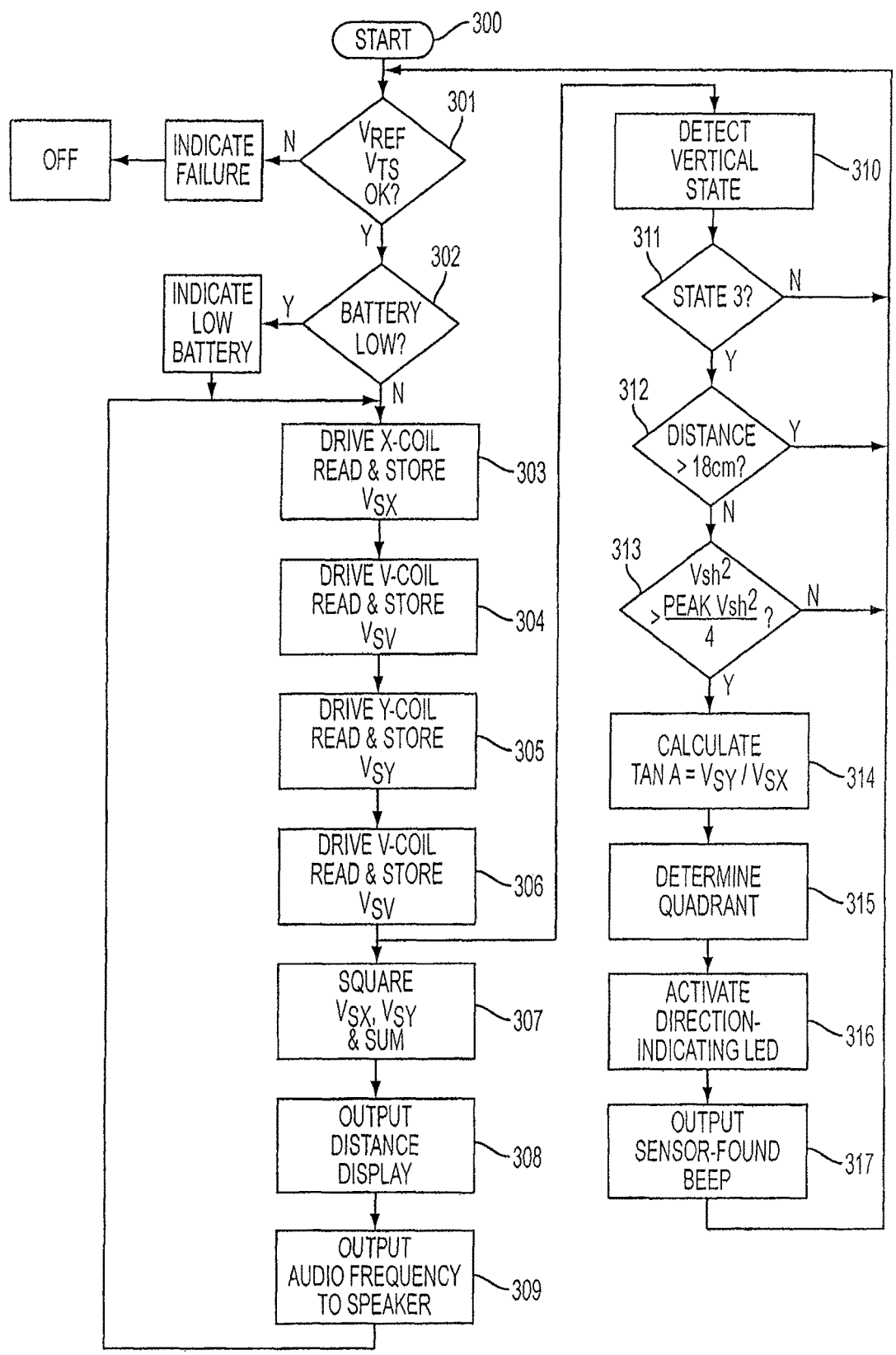
FIG. 23 is a flow chart illustrating the programming of the microprocessor of FIG. 20, and the operation of the system of FIG. 20.
Figure 25:
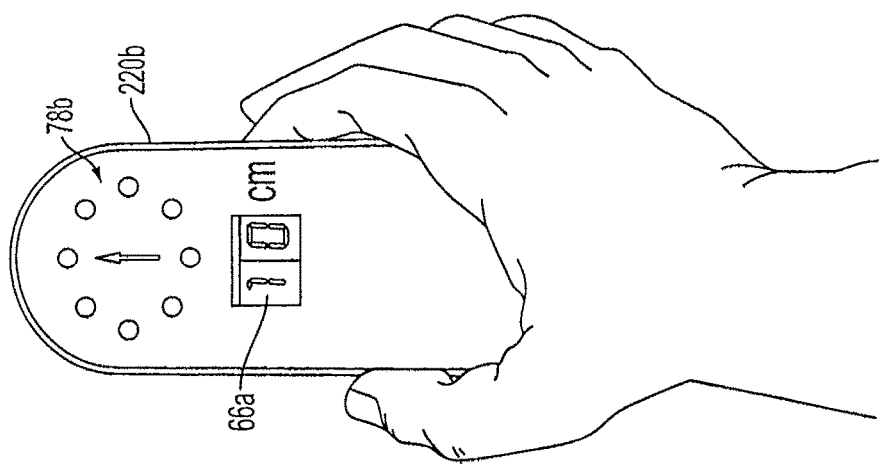
FIG. 25 is a top plan view of an alternative design for the noninvasive device of the system of this invention.

FIG. 23 is a flow diagram of the embodiment of the program resident in microprocessor 50, detailing the steps used to drive the three output coils, collect the sensor voltage level, make the necessary calculations and comparisons, and drive the audible and visual displays described above.

Start step 300 initializes all the storage registers and timers to zero, or to appropriate start up values. In step 301, multiplexer 46 is set by microprocessor 50 to select the reference DC voltage reference $V_{REF}$, and then select the amplified, rectified output of test sensor 130, Vts, and sequentially connect the voltages to A/D converter 48 shown in FIG. 20. If the values of the two voltages fall within preset limits, operation continues to step 302. Otherwise, a failure is indicated by alternately flashing the ON LED and the BATT.LOW LED for 15 seconds. The instrument is then shut off. In step 302, multiplexer 46 is connected by microprocessor 50 to the battery voltage Vbat. If Vbat is below a preset level, a low battery indicator, or LED, is activated by microprocessor 50. Operation would then continue to step 303.

In step 303, microprocessor 50 selects line X shown in FIG. 20 to drive X coil 105. Multiplexer 46 is enabled to select the amplified and rectified induced sensor voltage at the output of amplifier 40, which is digitized and stored in the memory of microprocessor 50. Steps 304, 305 and 306 repeat the process for the vertical coil by selecting line V out of the microprocessor 50, the Y coil by selecting line Y out of the microprocessor 50, and the vertical coil a second time, respectively.

In step 307, the signals induced by the X and Y coils are squared and summed by microprocessor 50 to produce a value which is based on the strength of the X and Y fields at the sensor, regardless of the sensor-to-output coil horizontal angle. In step 308, microprocessor 50 outputs from its lookup table digital information to drive decoder drivers 52 and 62 using the calculation as described above. At step 309, microprocessor 50 converts the values derived in step 307 to a variable frequency tone which drives speaker 44.

Steps 310 through 317 are the sensor coil location determination and direction display steps. In step 310, microprocessor 50 reads the value of the sensor coil voltage induced by the field generated from vertical output coil 122. Step 311 constitutes the microprocessor null detection subroutine for detecting the null in the output as shown in FIG. 19B. The microprocessor periodically reads and stores the peak value of the sensor voltage induced by the field from vertical output coil 122. Microprocessor 50 has established therein a threshold value which is a specific percentage of the peak vertical induced voltage. Typically, this threshold is set as ¼ of the peak voltage. Since the peak is continuously refreshed, this threshold may change. When the sensed voltage drops below this threshold, the microprocessor enters a second state—called state 2. After entering into the second state, if the vertical induced voltage again rises above the threshold by a predetermined amount, for example 50% above the threshold, state 3 is entered in step 311. If state 3 is entered, at step 312 the value of $Vsh^2$ is read. If the sensor-to-output coil distance determined from $Vsh^2$ is greater than a preset value (in this case 18 cm) the direction display is inhibited. This prevents the direction calculation from being based on weak induced signals which may have a large noise component and thus be inaccurate. In step 313, the microprocessor determines whether $Vsh^2$ exceeds the peak value of $Vsh^2$ divided by 4. If so, the tangent of angle A is calculated, step 314, the quadrant into which the sensor coil is pointing is determined, step 315, the appropriate direction-indicating LED is lit, step 316, and a "sensor found" audible beep is generated, step 317. This indicates to the operator that the sensor has been found. The direction calculation is performed only when the Vsv null has been detected (state 3). This is such that the Tangent A is calculated only when the XY output coil pair is closest to the sensor and at or near the plane of the sensor midpoint. This is where the tangent calculation is the most accurate.

As can be seen from FIG. 19B, if noninvasive device 220, which contains vertical coil 122, is moved back and forth relatively quickly while held at about 15 to 20 cm horizontally removed from the bisecting plane, at which there is a relative null in voltage $V_{sv}$, a false null may be simulated. That is, the voltage $V_{sv}$ can drop below the threshold and then rise again a percentage above the threshold. To reduce the likelihood of such a false null determination, microprocessor 50 is preferably programmed to require state 3 to occur within a specific required time interval after state 2 is entered, or else null detection is inhibited.

This state 2 to state 3 time interval is preferably variable with the strength of the peak voltage. For large sensor to output coil distances (depths), the peak signal is weak and the null is wide. That is, the voltage drops off relatively gradually as the vertical coil approaches plane P. In that case, a relatively long time interval is needed to allow the operator to move the instrument a sufficient distance to reach state 3. On the other hand, at shallow depths, the null becomes sharp and narrow. That is, the voltage drops off very rapidly when the output coil is very close to plane P. In this case, since the distance the noninvasive device must traverse to reach state 3 is small, the time interval can be short.

FIG. 19B illustrates this concept for three different catheter depths. At a depth of 10 cm, the noninvasive device must move from point A to point B to enter state 3. This equates to a distance of approximately 3 cm. If the noninvasive device is typically moved at 10 cm per second, the time interval to reach state 3 should be at least 0.3 seconds. At a depth of 20 cm, the distance from point C to point D is about 7 cm, which requires 0.7 seconds. Thus, the time interval should be at least 0.7 seconds. At shallow depths of 5 cm, only about 0.15 seconds is needed to traverse from point E to point F at the indicated speed. Thus, the time interval after state 2 is entered in which state 3 must be entered is preferably variable from about 0.15 to about 1.0 seconds. This time interval may be established by software in the microprocessor according to the peak value of Vsv using a lookup table.

In addition, the stored peak values of $Vsh^2$ and Vsv are preferably made to decay at a specific time constant, typically between 0.3 and 2.0 seconds. Decaying the Vsv peak helps to reduce false null determinations by continuously reducing the threshold values at distances remote from the sensor. If the decay time constant is too short, null detection can be inhibited if the operator is moving the instrument too slowly. If the decay constant is too long, false nulls can be indicated, if the operator moves the instrument back and forth at a horizontal distance of perhaps 15 to 20 cm from the sensor coil. Preferably the $Vsh^2$ peak is also decayed in a similar manner such that null detection will not be inhibited if the operator should move the instrument slightly farther vertically from the sensor, thereby reducing Vsv while the same threshold voltage is maintained.

In the embodiments described above, the noninvasive device 502, as shown in FIG. 1, for example, is able to communicate with the catheter assembly 504 through a changing magnetic field and also receive information relating the induced magnetic field in the coil 524. Therefore, the noninvasive device 502, which, in one embodiment, has no connecting wires or power cords, may be at least temporarily contained within a sterile bag or sheet (not shown) to protect the patient from substantial contamination that may exist with respect to the noninvasive device. Accordingly, the noninvasive device may be reused over a series of procedures with different patients while still facilitating a substantially sterile environment. Also, the lack of wires attached to the external housing of the noninvasive device 502 reduces the likelihood of wires becoming tangled with the medical personnel or other equipment during a medical procedure.

Although specific features of this embodiment are shown in some drawings and not others, this is for convenience only as each feature may be combined with any or all of the other features in accordance with the embodiment. It should be understood that various changes and modifications to the presently embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The embodiment is claimed as follows:

1. A catheter assembly configured to wirelessly communicate with a noninvasive device, the catheter assembly comprising:
   an invasive portion that is configured to be inserted into an animal;
   a noninvasive portion, which includes:
      a catheter extension;
      a connector;
      a processor; and
      a wireless transmitter operatively coupled to the processor;
   a sensor which is included in the invasive portion and is operatively coupled to the processor, the sensor being configured to, in response to a magnetic field being directed toward and reaching the sensor, output electric impulses;

a tube configured to support the sensor, the tube having an end member which is included in the invasive portion and is configured to be inserted into the animal;

an elongated conductor connected to the processor, wherein the connector is between the catheter extension and the tube, and the elongated conductor has a length that extends through the catheter extension, through the connector, and continues through the tube to the sensor; and a memory device which is included in the noninvasive portion, the memory device storing instructions which when executed by the processor, cause the processor, in cooperation with the sensor and the wireless transmitter, to:

(a) convert the electric impulses to a series of modulated radio waves; and (b) wirelessly transmit, from the wireless transmitter in the noninvasive portion outside the animal to the noninvasive device, the series of modulated radio waves, the noninvasive device being:
 (i) positionable over a surface of the animal; and
 (ii) separate from the catheter assembly.

2. The catheter assembly of claim 1, which includes a first battery operatively coupled to the processor.

3. The catheter assembly of claim 1, wherein the noninvasive portion further includes an indicator configured to indicate an operating parameter.

4. The catheter assembly of claim 3, wherein the operating parameter includes battery strength.

5. The catheter assembly of claim 1, wherein the end member includes a thermal energy ablation device.

6. The catheter assembly of claim 1, wherein the end member includes a stent.

7. The catheter assembly of claim 1, wherein the end member includes a balloon.

\* \* \* \* \*